United States Patent
Jacobsen et al.

(10) Patent No.: US 11,752,107 B2
(45) Date of Patent: Sep. 12, 2023

(54) 5-HYDROXYTRYPTOPHAN GASTRORETENTIVE DOSAGE FORMS

(71) Applicant: Evecxia Therapeutics, Inc., Research Triangle Park, NC (US)

(72) Inventors: Jacob Pade Ramsoe Jacobsen, Durham, NC (US); Bret Berner, Seattle, WA (US); Wu Lin, Nottingham (GB); Ching Sieu Tay, Nottingham (GB)

(73) Assignee: Evecxia Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 17/877,699

(22) Filed: Jul. 29, 2022

(65) Prior Publication Data

US 2023/0047338 A1    Feb. 16, 2023

Related U.S. Application Data

(60) Provisional application No. 63/227,915, filed on Jul. 30, 2021.

(51) Int. Cl.
*A61K 9/20* (2006.01)
*A61K 31/197* (2006.01)
*A61K 31/405* (2006.01)
*A61K 9/24* (2006.01)

(52) U.S. Cl.
CPC .......... *A61K 9/2086* (2013.01); *A61K 9/2054* (2013.01); *A61K 31/197* (2013.01); *A61K 31/405* (2013.01)

(58) Field of Classification Search
None
See application file for complete search history.

(56) References Cited

U.S. PATENT DOCUMENTS

| | | |
|---|---|---|
| 4,140,755 A | 2/1979 | Sheth et al. |
| 4,191,184 A | 3/1980 | Carlisle |
| 4,658,038 A | 4/1987 | Tamir et al. |
| 4,996,058 A | 2/1991 | Sinnreich |
| 6,340,475 B2 | 1/2002 | Shell et al. |
| 6,475,521 B1 | 11/2002 | Timmins et al. |
| 6,488,962 B1 | 12/2002 | Berner et al. |
| 6,635,280 B2 | 10/2003 | Shell et al. |
| 6,723,340 B2 | 4/2004 | Gusler et al. |
| 6,960,356 B1 | 11/2005 | Talwar et al. |
| 7,094,427 B2 | 8/2006 | Han et al. |
| 7,101,912 B2 | 9/2006 | Xiang et al. |
| 7,438,927 B2 | 10/2008 | Berner et al. |
| 7,670,619 B2 | 3/2010 | Mihaylov |
| 7,674,480 B2 | 3/2010 | Fleshner-Barak et al. |
| 7,765,989 B2 | 8/2010 | Maruyama |
| 8,771,730 B2 | 7/2014 | Navon et al. |
| 8,778,396 B2 | 7/2014 | Pillay et al. |
| 8,969,400 B2 | 3/2015 | Jacobsen et al. |
| 9,161,911 B2 | 10/2015 | Hou |
| 9,468,627 B2 | 10/2016 | Jacobsen et al. |
| 9,980,903 B2 | 5/2018 | Berner et al. |
| 11,337,963 B2 | 5/2022 | Jacobsen et al. |
| 2006/0013875 A1 | 1/2006 | Han et al. |
| 2008/0268045 A1 | 10/2008 | Dervieux et al. |
| 2011/0287096 A1 | 11/2011 | Gorukanti et al. |
| 2013/0230577 A1 | 9/2013 | Jacobsen et al. |
| 2017/0266112 A1 | 9/2017 | Bellinger et al. |
| 2018/0311154 A1 | 11/2018 | Kanasty et al. |
| 2021/0361566 A1* | 11/2021 | Jacobsen .............. A61K 9/2077 |

FOREIGN PATENT DOCUMENTS

| | | | |
|---|---|---|---|
| CN | 103554005 A | 11/2013 | |
| EP | 1382331 A1 * | 1/2004 | ........... A61K 9/2086 |
| WO | WO 1991/07960 | 6/1991 | |
| WO | WO 2004/028512 A1 | 4/2004 | |
| WO | WO-2004028512 A1 * | 4/2004 | ........... A61K 9/0004 |
| WO | WO 2008/100107 A1 | 8/2008 | |
| WO | WO 2011/151708 A1 | 12/2011 | |
| WO | WO 2019/148087 A1 | 8/2019 | |
| WO | WO-2019148087 A1 * | 8/2019 | ........... A61K 31/135 |
| WO | WO-2019245925 A1 * | 12/2019 | ........... A61K 31/405 |
| WO | WO2020/014334 A1 | 1/2020 | |

OTHER PUBLICATIONS

Agren et al., "Low brain uptake of L-[11C]5-hydroxytryptophan in major depression: a positron emission tomography study on patients and healthy volunteers." Acata Psychiatr. Scand., vol. 83(6), pp. 449-455 (1991).

Alino et al., "5-Hydroxytryptophan (5-HTP) and a MAOI (nialamide) in the treatment of depressions. A double-blind controlled study." Int. Pharmacopsychiatry, vol. 11(1), pp. 8-15 (1976).

Allen GF, Land JM, Heales SJ (2009) "A new perspective on the treatment of aromatic L-amino acid decarboxylase deficiency," Mol Genet Metab 97(1): 6-14.

Appleby et al., "A controlled study of fluoxetine and cognitive-behavioral counselling in the treatment of postnatal depression." Bmj, vol. 314, pp. 932-936 (1997).

Asberg, "Neurotransmitters and suicidal behavior. The evidence from cerebrospinal fluid studies." Ann. NY Acad. Sci., vol. 836, pp. 158-181 (1997).

Attenburrow et al., (2001). "Low-dose citalopram as a 5-HT neuroendocrine probe," Psychopharmacology 155(3): pp. 323-326.

Badawy et al., "Tryptophan Metabolism in Rat Liver After Administration of Tryptophan, Kynurenine Metabolites, and Kynureninase Inhibitors." Int. J. Tryptophan Res., vol. 9, pp. 51-65 (2016).

(Continued)

*Primary Examiner* — Susan T Tran

(74) *Attorney, Agent, or Firm* — Jenkins, Taylor & Hunt, P.A.

(57) ABSTRACT

A gastroretentive, sustained-release dosage form including 5-hydroxytryptophan (5-HTP) as an active ingredient and low-dose carbidopa is described. For example, the dosage form can be provided as a bilayer tablet comprising a swelling layer and a modified release layer, where the 5-HTP and carbidopa are both included in the modified release layer. The dosage form provides for essentially parallel release of the 5-HTP and the carbidopa with, for instance, release of 80% of the 5-HTP and carbidopa at about 5 hours to about 12 hours.

28 Claims, 14 Drawing Sheets

(56) References Cited

OTHER PUBLICATIONS

Bartels et al., "Impact of SSRI Therapy on Risk of Conversion From Mild Cognitive Impairment to Alzheimer's dementia in Individuals With Previous Depression." Am. J. Psychiatry, vol. 175(3), pp. 232-241 (2018).

Beaulieu et al., "Role of GSK3 beta in behavioral abnormalities induced by serotonin deficiency." Proceedings of the National Academy of Sciences of the United States of America, vol. 105(4), pp. 1333-1338 (2008).

Birdsall et al., "5-Hydroxytryptophan: a clinically-effective serotonin precursor." Altern. Med. Rev., vol. 3(4), pp. 271-280 (1998).

Blier et al., "Current advances and trends in the treatment of depression." Trends in Pharmacological Sciences, vol. 15(7), pp. 220-226 (1994).

Blier et al., "Sequential administration of augmentation strategies in treatment-resistant obsessive-compulsive disorder: preliminary findings." Int. Clin. Psychopharmacol., vol. 11(1), pp. 37-44 (1996).

Bono G, et al. (1984) "L-5HTP treatment in primary headaches: an attempt at clinical identification of responsive patients," Cephalalgia 4(3): 159-165.

Bowsher et al., "Aromatic L-Amino Acid Decarboxylase. In: Boulton et al.," Neurotransmitter Enzymes. Neuromethods, Humana Press, vol. 5, 46 pages (1986).

Brown et al., "Aggression, suicide, and serotonin: relationships to CSF amine metabolites." Am. J. Psychiatry, vol. 139(6), pp. 741-746 (1982).

Bruni et al., "L-5-Hydroxytrytophan treatment of sleep terrors in children." Eur. J. Pediatr., vol. 163(7), pp. 402-407 (2004).

Byerley et al., "5-Hydroxytryptophan: a review of its antidepressant efficacy and adverse effects." J. Clin. Psychopharmacol., vol. 7(3), pp. 127-137 (1987).

Cangiano et al., "Eating behavior and adherence to dietary prescriptions in obese adult subjects treated with 5-hydroxytrytophan." Am. J. Clin. Nutr., vol. 56(5), pp. 863-867 (1993).

Caruso et al., "Double-blind study of 5-Hydroxytrytophan versus placebo in the treatment of primary fibromyalgia syndrome." The Journal of International Medical Research, vol. 18(3), pp. 201-209 (1990).

Carver et al., "Serotonergic function, two-mode models of self-regulation, and vulnerability to depression: what depression has in common with impulsive aggression." Psychol. Bull., vol. 134(6), pp. 912-943 (2008).

Claxton et al., "A systematic review of the associations between dose regimens and medication compliance." Clinical Therapeutics, vol. 23(8), pp. 1296-1310 (2001).

Connor et al., "Fluoxetine in post-traumatic stress disorder." Randomised, double-blind study. Br. J. Psychiatry, vol. 175, pp. 17-22 (1999).

Coric et al., "Multicenter, randomized, double-blind, active comparator and placebo-controlled trial of a corticotropin-released factor receptor-1 antagonist in generalized anxiety disorder." Depress. Anxiety, vol. 27(5), pp. 417-425 (2010).

Da Prada et al., "Inhibition of Decarboxylase and Levels of Dopa and 3-O-Methyldopa: A Comparative Study of Benserazide versus Carbidopa in Rodents and of Madopar Standard versus Madopar HBS in Volunteers." Eur. Neurol., vol. 27(Suppl. 1), pp. 9-20 (1987).

Donnelly, Ronald F (2016) "Stability of Levodopa/Carbidopa Rectal Suspensions," Hosp Pharm. Dec; 51(11): pp. 915-921.

Demisch K, et al. (1986) "Melatonin and cortisol increase after fluvoxamine," British journal of clinical pharmacology 22(5): 620-622.

Dulay MS, Dulay JS (2020) "Antiemetics: types, actions and use," Br J Hosp Med (Lond) 81(5): 1-8.

Eisenhofer G et al. (2014) "Levodopa therapy in Parkinson's disease: influence on liquid chromatographic tandem mass spectrometric-based measurements of plasma and urinary normetanephrine, metanephrine and methoxytyramine," Ann Clin Biochem 51(Pt 1): pp. 38-46.

Extended European Search Report Corresponding to European Application No. 19823684.6 dated Feb. 23, 2022.

FDA (2022). "Assessing the Effects of Food on Drugs in INDs and NDAs—Clinical Pharmacology Considerations Guidance for Industry," 18 Pages.

Freitas et al., "Novel Levodopa Formulations for Parkinson's Disease." CNS Drugs, vol. 30(11), pp. 1079-1095 (2016).

Fu DJ, et al (2020), "Esketamine Nasal Spray for Rapid Reduction of Major Depressive Disorder Symptoms in Patients Who Have Active Suicidal Ideation With Intent: Double-Blind, Randomized Study (ASPIRE I)," J Clin Psychiatry 81(3). pp. 22-31.

Fuller et al., "Effect of serotonin-releasing drugs on serum corticosterone concentration in rats." Neuroendocrinology, vol. 31(2), pp. 96-100 (1980).

Garfinkel PE, et al. (1977) "The effect of a peripheral decarboxylase inhibitor (carbidopa) on monoamine and neuroendocrine function in man," Neurology 27(5): 443-447.

Gasser et al., "Pharmaceutical quality of seven generic Levodopa/Benserazide products compared with original Madopar®/Prolopa®." BMC Pharmacol. Toxicol., vol. 14, p. 24 (2013).

Gershon, "5-Hydroxytryptamine (serotonin) in the gastrointestinal tract." Curr. Opin. Endocrinol. Diabetes Obes., vol. 20(1), pp. 14-21 (2013).

Gibbons RD et al. (2012) "Suicidal Thoughts and Behavior With Antidepressant Treatment: Reanalysis of the Randomized Placebo-Controlled Studies of Fluoxetine and Venlafaxine," Archives of general psychiatry. 69(6): 15 Pages.

Gijsman et al., "Placebo-controlled comparison of three dose-regimens of 5-hydroxytryptophan challenge test in healthy volunteers." J. Clin. Psychopharmacol., vol. 22(2), pp. 183-189 (2002).

Guan Z, (2020). "PK/PD modeling of 5-hydroxytryptophan (5-HTP) challenge test with cortisol measurement in serum and saliva" Pharmacol Res Perspect 8(2): e00574.

Guerdjikova et al., High-dose escitalopram in the treatment of binge-eating disorder with obesity: a placebo-controlled monotherapy trial. Hum. Psychopharmacol., vol. 23(1), pp. 1-11 (2008).

Haahr ME, et al (2014) "Central 5-HT4 receptor binding as biomarker of serotonergic tonus in humans: a [11C]SB207145 PET study," Mol Psychiatry 19(4): 427-432.

Haddad, P (1998) The SSRI discontinuation syndrome. J Psychopharmacol. 12(3):305-13.

Hsu et al.,(2015) "Comparison of the pharmacokinetics of an oral extended-release capsule formulation of carbidopa-levodopa (IPX066) with immediate-release carbidopa-levodopa (Sinemet®), sustained-release carbidopa-levodopa (Sinemet® CR), and carbide-levodopa-entacapone (Stalveto®)." Journal of Clinical Pharmacol., pp. 995-1003.

Hua et al., "Advances in oral nano-delivery systems for colon targeted drug delivery in inflammatory bowel disease: selective targeting to diseased versus healthy tissue." Nanomedicine, vol. 11(5), pp. 1117-1132 (2015).

International Preliminary Report on Patentability Corresponding to International application No. PCT/US 2019/037349 dated Dec. 22, 2020.

International Search Report and Written Opinion corresponding to US. Patent application No. PCT/US2022/038914 dated Nov. 22, 2022.

International Search Report and Written Opinion of the International Searching Authority Corresponding to International application No. PCT/US 2019/037349 dated Aug. 27, 2019.

Jackson et al., "Pharmacotherapy of eating disorders." Nutr. Clin. Pract., vol. 25(2), pp. 143-159 (2010).

Jacobsen et al., "Adjunctive 5-Hydroxytryptophan Slow-Release for Treatment-Resistant Depression: Clinical and Preclinical Rationale." Trends Pharmacol. Sci., vol. 37(11), pp. 933-944 (2016).

Jacobsen et al., "Deficient serotonin neurotransmission and depression-like serotonin biomarker alterations in tryptophan hydroxylase 2 (Tph2) loss-of-function mice." Molecular Psychiatry, vol. 17(7), pp. 694-704 (2012).

(56) References Cited

OTHER PUBLICATIONS

Jacobsen et al., "SSRI Augmentation by 5-Hydroxytryptophan Slow Release: Mouse Pharmacodynamic Proof of Concept." Neuropsychopharmacology, vol. 41(9), pp. 2324-2334 (2016).
Jacobsen et al., "The 5-HT deficiency theory of depression: perspectives from a naturalistic 5-HT deficiency model, the tryptophan hydroxylase 2Arg439His knockin mouse." Philos. Trans. R. Soc. Lond. B. Biol. Sci., vol. 367, pp. 2444-2456 (2012).
Jacobsen JPR, et al (2019). "Slow-release delivery enhances the pharmacological properties of oral 5-hydroxytryptophan: mouse proof-of-concept," Neuropsychopharmacology 44(12): pp. 2082-2090.
Kahn et al., "Effect of a serotonin precursor and uptake inhibitor in anxiety disorders: a double-blind comparison of 5-hydroxytryptophan, clomipramine and placebo." Int. Clin. Psychopharmacol., vol. 2(1), pp. 33-45 (1987).
Kahn RS, Westenberg HG (1985) "L-5-hydroxytryptophan in the treatment of anxiety disorders," J Affect Disord 8(2): 197-200.
Kelwala S, et al. (1983) "History of antidepressants: successes and failures," The Journal of clinical psychiatry 44(5 Pt 2): 40-48.
Kapitany T, Schindl M, Schindler SD, Hesselmann B, Fureder T, Barnas C, et al (1999). The citalopram challenge test in patients with major depression and in healthy controls. Psychiatry Res 88(2): 75-88.
Lader et al., "Efficacy and tolerability of escitalopram in 12- and 24-week treatment of social anxiety disorder: randomized, double-blind, placebo-controlled, fixed-dose study." Depress. Anxiety, vol. 19(4), pp. 241-248 (2004).
Levy A, Chen R (2016) "Myoclonus: Pathophysiology and Treatment Options," Curr Treat Options Neurol 18(5): 21.
Lopes et al., "Overview on gastroretentive drug delivery systems for improving drug bioavailability." Int. J. Pharm., vol. 510(1), pp. 144-158 (2016).
Lowe et al., "L-5-Hydroxytryptophan augments the neuroendocrine response to a SSRI." Psychoneuroendocrinology, vol. 31(4), pp. 473-484 (2006).
Mashchak CA, Kletzky OA, Spencer C, Artal R (1983). Transient effect of L-5-hydroxytryptophan on pituitary function in men and women. J Clin Endocrinol Metab 56(1): 170-176.
Magnussen I, et al. (1977) "Palatal myoclonus treated with 5-hydroxytryptophan and a decarboxylase-inhibitor," Acta Neurol Scand 55(3): 251-253.
Magnussen I, Mondrup K, Engbaek F, Lademann A, Olivarius BD (1982) "Treatment of myoclonic syndromes with paroxetine alone or combined with 5-HTP," Acta Neurol Scand 66(2): 276-282.
Manegold et al., "Aromatic L-amino acid decarboxylase deficiency: clinical features, drug therapy and follow-up." J. Inherit. Metab. Dis., vol. 32(3), pp. 371-380 (2009).
Mead et al., "Selective serotonin reuptake inhibitors for stroke recovery: a systematic review and meta-analysis." Stroke, vol. 44(3), pp. 844-850 (2013).
Meloni M, et al (2020b). "Efficacy and safety of 5-Hydroxytryptophan on levodopa-induced motor complications in Parkinson's disease: A preliminary finding." J Neurol Sci 415: 116869.
Meloni M, et al. (2020a). "Efficacy and safety of 5-hydroxytryptophan on depression and apathy in Parkinson's disease: a preliminary finding." Eur J Neurol 27(5): 779-786.
Meltzer H, et al. (1997) "Fluoxetine, but not tricyclic antidepressants, potentiates the 5-hydroxytryptophan-mediated increase in plasma cortisol and prolactin secretion in subjects with major depression or with obsessive compulsive disorder," Neuropsychopharmacology 17(1): pp. 1-11.
Meltzer HY, (1983) "Enhanced serum cortisol response to 5-hydroxytryptophan in depression and mania," Life Sci 33(25): 2541-2549.
Merck, Sinemet CR, Merck Sharp & Dohme Corp., 12 pages (2018).
Mitra et al., "Feasibility of mini-tablets as a flexible drug delivery tool." Int. J. Pharm., vol. 525(1), pp. 149-159 (2017).

Murphy TK, et al. (2008) "SSRI adverse events: how to monitor and manage. International review of psychiatry," (Abingdon, England) 20(2): 203-208.
Nicolodi et al., "L-5-Hydroxytryptophan can prevent nociceptive disorders in man." Adv. Exp. Med. Biol., vol. 467, pp. 177-182 (1999).
Nokhodchi et al., "The role of oral controlled release matrix tablets in drug delivery systems." Bioimpacts, vol. 2(4), pp. 175-187 (2012).
Nord M, et al. (2013) "Effect of a single dose of escitalopram on serotonin concentration in the non-human and human primate brain," Int J Neuropsychopharmacol 16(7): pp. 1577-1586.
Office Action (Restriction Requirement) corresponding to U.S. Appl. No. 17/252,961 dated Jan. 18, 2022.
Office Action corresponding to Israeli Patent Application No. 279509 dated Aug. 1, 2021.
Office Action corresponding to U.S. Appl. No. 17/252,961 dated Apr. 14, 2022.
Office Action corresponding to Vietnamese Application No. 1-2020-07497 dated Apr. 27, 2021.
Oquendo MA, et al (2014), "Toward a Biosignature for Suicide," Am J Psychiatry. 171(12); pp. 1-33.
Pahwa et al., "Randomized trial of IPX066, carbidopa/levodopa extended release, in early Parkinson's disease." Parkinsonism Relat. Disord., vol. 20(2), pp. 142-148 (2014).
Pereira VS, et al. (2018), "A brief history of antidepressant drug development from tricyclics to beyond ketamine," Acta Neuropsychiatr 30(6): 307-322.
Perry et al., "Extracellular 5-hydroxytryptamine concentration in rat hypothalamus after administration of fluoxetine plus L-5-hydroxytryptophan." J. Pharm. Pharmacol., vol. 45(8), pp. 759-761 (1993).
Rao N (2007). "The clinical pharmacokinetics of escitalopram." Clin Pharmacokinet 46(4): pp. 281-290.
Rauws et al., "Comparative 90-day toxicity of two decarboxylase inhibitors, benserazide and carbidopa, in the rat." Toxicol. Appl. Pharmacol., vol. 66(2), pp. 201-220 (1982).
Rose et al., "The effect of carbidopa on plasma and muscle levels of L-dopa, dopamine, and their metabolites following L-dopa administration to rats." Mov. Disord., vol. 3(2), pp. 117-125 (1988).
Santucci M, et al. (1986) "L-5-hydroxytryptophan versus placebo in childhood migraine prophylaxis: a double-blind crossover study," Cephalalgia 6(3): 155-157.
Sargent et al., "Brain 5-HT neurotransmission during paroxetine treatment." Br. J. Psych., vol. 172, pp. 49-52 (1998).
Sharma et al., "To scale or not to scale: the principles of dose exploration." Br. J. Pharmacol., vol. 157(6), pp. 907-921 (2009).
Shenker Y, et al. (1985) "Central serotonergic stimulation of aldosterone secretion," J Clin Invest 76(4): pp. 1485-1490.
Shindo et al., "Mechanism of intestinal absorption and brain uptake of L-5-hydroxytryptophan in rats, as compared to those of L-3,4-dihydroxyphenylalanine." Chem. Pharm. Bull. (Tokyo), pp. 25(6), pp. 1417-1425 (1977).
Smith BP, et al (2000). "Confidence interval criteria for assessment of dose proportionality," Pharm Res 17(10): pp. 1278-1283.
Sloan et al., "Fluoxetine as a treatment for emotional lability after brain injury." Brain Inj., vol. 6(4), pp. 315-319 (1992).
Smarius LJ, et al (2008) "Pharmacology of rising oral doses of 5-hydroxytryptophan with carbidopa." J Psychopharmacol 22(4): 426-433.
Soulairac et al., "Effect of 5-hydroxytryptophan, a serotonin precursor, on sleep disorders." Ann. Med. Physchol. (Paris), vol. 1(5), pp. 792-798 (1977).
Steiner et al., "Fluoxetine in the treatment of premenstrual dysphoria. Canadian Fluoxetine/Premenstrual Dysphoria Collaborative Study Group." N. Engl. J. Med., vol. 332(32), pp. 1529-1534 (1995).
Sutton, "The use of gastrointestinal intubation studies for controlled release development." Br. J. Clin. Pharmacol, vol. 68(3), pp. 342-354 (2009).
Takahashi et al., "Measurement of 5-hydroxyindole compounds during L-5-HTP treatment in depressed patients." Folia. Psychiatr. Neurol. Jpn., vol. 30(4), pp. 463-473 (1976).

(56) References Cited

OTHER PUBLICATIONS

Tang SJ, (2002) "The novel use of an intravenous proton pump inhibitor in a patient with short bowel syndrome," J Clin Gastroenterol 34(1): 62-63.

Taylor MJ, et al. (2006) "Early onset of selective serotonin reuptake inhibitor antidepressant action: systematic review and meta-analysis," Arch Gen Psychiatry 63(11): pp. 1-15 Pages.

Thombre AG (2005). Assessment of the feasibility of oral controlled release in an exploratory development setting. Drug Discov Today 10(17): 1159-1166.

Thombre et al., "Osmotic drug delivery using swellable-core technology." J. Control Release, vol. 94(1), pp. 75-89 (2004).

Timmermans et al., "Factors controlling the buoyancy and gastric retention capabilities of floating matrix capsules: New data for reconsidering the controversy." J. Pharm. Sci., vol. 83, pp. 18-24 (1994).

Trivedi MH, et al (2006) "Evaluation of outcomes with citalopram for depression using measurement-based care in STAR*D: implications for clinical practice," The American journal of psychiatry 163(1): pp. 28-40.

Trouillas et al., "Improvement of cerebellar ataxia with levorotatory form of 5-hydroxytryptophan. A double-blind study with quantified data processing." Arch. Neurol., vol. 45(11), pp. 1217-1222 (1988).

Turner et al., "Serotonin a la carte: supplementation with the serotonin precursor 5-hydroxytryptophan." Pharmacol. Ther., vol. 109(3), pp. 325-338 (2006).

Van Hiele, L-5-Hydroxytryptophan in depression: the first substitution therapy in psychiatry? The treatment of 99 out-patients with "therapy resistant" depressions. Neuropsychobiology. vol. 6(4), pp. 230-240 (1980).

Van Praag, "Serotonin precursors in the treatment of depression." Adv. Biochem. Psychopharmacol., vol. 34, pp. 259-286 (1982).

Van Woert et al., "Long-term therapy of myoclonus and other neurologic disorders with L-5-hydroxytryptophan and carbidopa." N. Engl. J. Med., vol. 296(2), pp. 70-75 (1977).

Van Vliet et al. (1996) "Behavioral, neuroendocrine and biochemical effects of different doses of 5-HTP in panic disorder," European neuropsychopharmacology : the journal of the European College of Neuropsychopharmacology 6(2): 103-110.

Veenstra-VanderWeele et al., "Autism gene variant causes hyperserotonemia, serotonin receptor hypersensitivity, social impairment and repetitive behavior." Proc. Natl. Acad. Sci. USA, vol. 109(14), pp. 5469-5474 (2012).

Verhagen Metman et al., "Gastroretentive carbidopa/levodopa, DM-1992, for the treatment of advanced Parkinson's disease." Mov. Disord., vol. 30(9), pp. 1222-1228 (2015).

Viglliante I, et al. (2019). "Chemical Characterization and DNA Fingerprinting of Griffonia simplicifolia Baill," Molecules 24(6);pp. 1-9.

Viscogliosi et al., "Efficacy and Safety of Citalopram Compared to Atypical Antipsychotics on Agitation in Nursing Home Residents With Alzheimer Dementia." J. Am. Med. Dir. Assoc., vol. 18(9), pp. 799-802 (2017).

Westenberg et al., "Kinetics of L-5-hydroxytryptophan in healthy subjects." Psychiatry Res., vol. 7(3), pp. 373-385 (1982).

Yeh et al., "Pharmacokinetics and bioavailability of Sinemet CR: A summary of human studies," Neurology, vol. 39(Suppl. 2), pp. 25-38 (1989).

Yoshimura et al., "Involvement of dopamine in development of hypertension in spontaneously hypertensive rat effect of carbidopa, inhibitor of peripheral dopa decarboxylase." Clin. Exp. Hypertens. A., vol. 9(10), pp. 1585-1599 (1987).

Yousefzadeh F, et al (2020), "5-Hydroxytryptophan as adjuvant therapy in treatment of moderate to severe obsessive-compulsive disorder: a double-blind randomized trial with placebo control," elnt Clin Psychopharmacol.

Zalsman G, et al (2016). "Suicide prevention strategies revisited: 10-year systematic review," Lancet Psychiatry 3(7): 646-659.

* cited by examiner

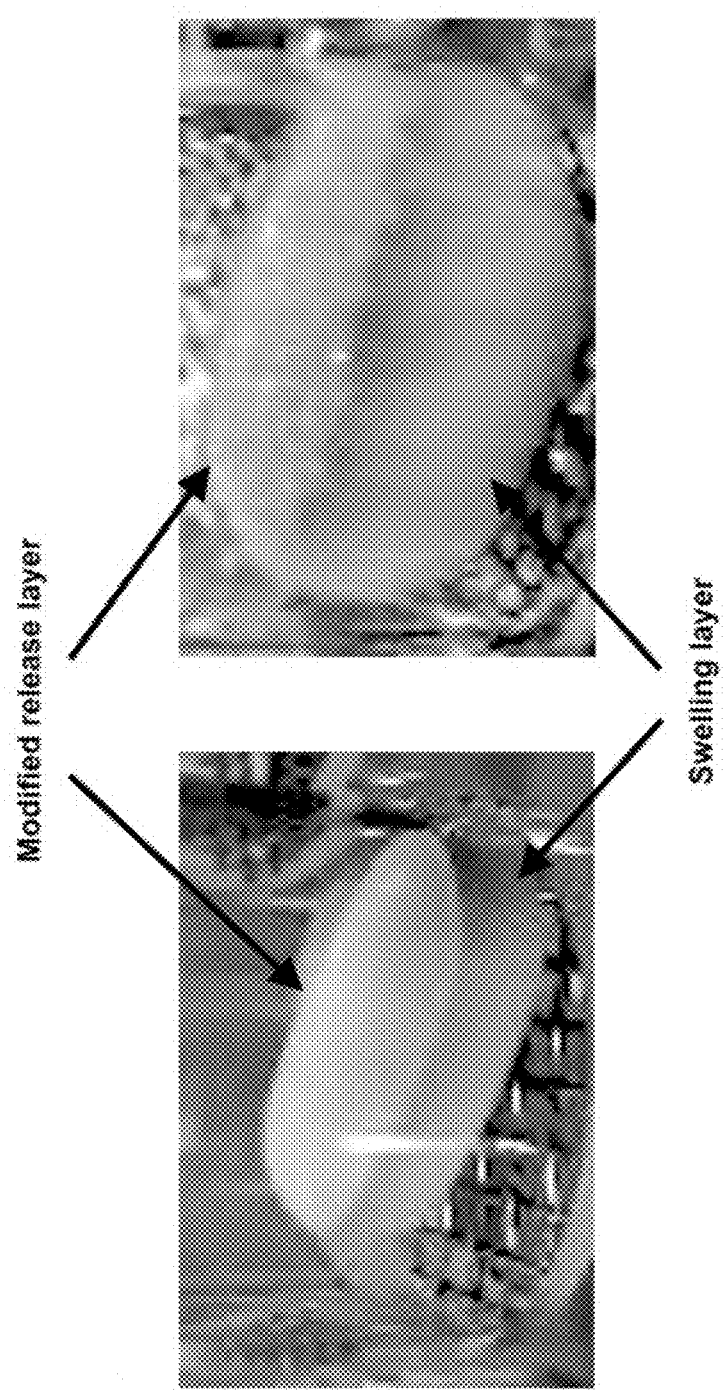

5-HYDROXYTRYPTOPHAN GASTRORETENTIVE DOSAGE FORMS

CROSS REFERENCE TO RELATED APPLICATIONS

This application claims priority to and the benefit of U.S. Provisional Patent Application Ser. No. 63/227,915, filed Jul. 30, 2021; the disclosure of which is incorporated herein by reference in its entirety.

TECHNICAL FIELD

The presently disclosed subject matter relates to gastroretentive, sustained-release dosage forms for 5-hydroxytryptophan (5-HTP) and to methods of treating disorders of the body using said dosage forms.

BACKGROUND

The listing or discussion of an apparently prior-published document in this specification should not necessarily be taken as an acknowledgement that the document is part of the state of the art or is common general knowledge.

5-Hydroxytryptophan (5-HTP) is the natural rate-limiting precursor of serotonin in the mammalian body (Jacobsen et al, 2016b). Serotonin is a signaling molecule, present in many tissues of the body, including the brain and the intestine. Oral administration of exogenous 5-HTP to the mammalian body can increase plasma levels of 5-HTP and brain levels of serotonin (Jacobsen et al, 2016b). In humans, 5-HTP has been used experimentally to treat depression (van Praag, 1982), anxiety (Kahn and Westenberg, 1985), myoclonus (Magnussen et al, 1977), fibromyalgia (Caruso et al, 1990), migraine (Santucci et al, 1986), headache (Bono et al, 1984), obesity (Cangiano et al, 1992), Parkinson's Disease depression (Meloni et al, 2020a), L-DOPA dyskinesias in Parkinson's Disease (Meloni et al, 2020b), sleep disorders (Birdsall, 1998), certain pediatric developmental disorders (Ramaekers et al, 2001), and ataxic disorders (Trouillas et al, 1988), among other diseases.

A 5-HTP medication could also have therapeutic relevance in indications known to be responsive to pro-serotonergics, non-limiting examples of which include social anxiety, panic disorder, generalized anxiety disorder, obsessive compulsive disorder (OCD), mood symptoms and agitation related to neurological disorders (e.g. Alzheimer's, Parkinson's), stroke recovery, premenstrual dysphoria, post-traumatic stress disorder, post-partum depression, depression after interferon treatment, eating disorders, obesity, irritable bowel syndrome-constipation, idiopathic constipation, and other constipation disorders. Moreover, a 5-HTP medication could have therapeutic relevance in indications where the pathogenesis is associated with low brain serotonin, non-limiting examples of which include impulse control disorders, aggression, suicidality, borderline personality disorder, autism, phenylketonuria, and tetrahydrobiopterin deficiency.

However, native 5-HTP in an immediate release dosage form (hereinafter "native 5-HTP immediate release", i.e., the naturally occurring molecular form of 5-HTP formulated for immediate release without compounds that can enhance 5-HTP bioavailability) has inadequate pharmacokinetics for practical therapeutic use. For example, native 5-HTP immediate release has a short half-life ($T_{1/2}$~2 h; typically reported to be 1.5 h to 3 h (Gijsman et al, 2002)), which necessitates frequent dosing, e.g., 3 or more times per day, to provide reasonably stable exposure (Thombre, 2005; van Praag, 1982). Further, native 5-HTP immediate release has rapid absorption ($T_{Max}$~1 h), which is associated with rapid $C_{Max}$-related adverse events (Lowe et al, 2006; van Praag, 1982). In addition, in many therapeutic scenarios, the modest oral bioavailability of native 5-HTP immediate release (e.g., in one study ~20% (WO2019245925)) can lead to the use of high daily doses, and hence large dosage forms, or many dosage forms ingested per day, which can make therapy cumbersome or impractical.

Animal data demonstrate that sustained-release 5-HTP administration (modeled using either osmotic minipumps or dietary administration) can: (i) provide sustained elevated 5-HTP plasma levels; (ii) enhance brain serotonin synthesis, levels, and function; and (iii) markedly reduce the adverse events usually associated with native 5-HTP immediate release. In addition, the animal data imply that the adverse events associated with native 5-HTP immediate release administration is not only associated with 5-HTP plasma $C_{Max}$, but also with the steepness of the slope to $C_{Max}$ (Jacobsen et al, 2016a; Jacobsen et al, 2019).

Thus, there is a need for a sustained-release drug technology for 5-HTP, e.g., dosage forms that can substantially delay 5-HTP plasma $T_{Max}$, hence decreasing the steepness of the slope to $C_{Max}$, compared to what is observed with native 5-HTP immediate release administration and/or that can provide for maintained 5-HTP plasma levels within the therapeutical range, ideally once- or twice-daily dosing. Such technology could have wide therapeutic relevance across CNS and non-CNS disorders, e.g., by providing more effective ability to elevate endogenous serotonin synthesis, serotonin levels (intra- and/or extracellular), serotonin neurotransmission, and serotonin function, in the brain or periphery, depending on the indication. Dosage forms based on such technology could be used as a monotherapy or as an adjunctive therapy for other pro-serotonergics, e.g., as an adjunctive therapy for serotonin reuptake inhibitors. Further, such dosage forms could be used as an adjunctive therapy to other therapies that have only partial or no serotonin modulatory pharmacology.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a gastroretentive dosage form comprising a tablet, wherein said tablet comprises two layers: (a) a swelling layer comprising one or more hydrophilic polymers, wherein each of said one or more hydrophilic polymers is swellable in the presence of gastric fluid; and (b) a modified release layer, wherein the modified release layer comprises 5-hydroxytryptophan (5-HTP) and carbidopa; and wherein a time period for 80% by weight of the 5-HTP to release from the dosage form in dissolution testing is within about 2 hours of a time period for release of 80% by weight percentage of the carbidopa. In some embodiments, the time period for 80% by weight of one or both of the 5-HTP and the carbidopa to release from the dosage form in dissolution testing is about 5 hours to about 12 hours.

In some embodiments, the modified release layer comprises one or more hydrophilic polymers selected from the group comprising a low viscosity hydroxypropyl methylcellulose (HPMC), medium viscosity HPMC, high viscosity HPMC, low molecular weight (MW) polyethylene oxide (PEO), medium MW PEO, high MW PEO, and high viscosity hydroxyethyl cellulose. In some embodiments, the modified release layer comprises about 14% (w/w) to about 37% (w/w) of the one or more hydrophilic polymers based on a total weight of the modified release layer. In some embodiments, the modified release layer comprises about 5% (w/w) of a medium MW PEO or a high MW PEO and about 13% (w/w) to about 32% (w/w) of a low viscosity HMPC, a medium viscosity HPMC, or a mixture of medium viscosity HPMC and high viscosity HPMC based on a total weight of the modified release layer.

In some embodiments, the modified release layer comprises, based on a total weight of the modified release layer: (i) about 50% (w/w) 5-HTP; (ii) about 0.0625% (w/w) to about 5% (w/w) carbidopa; or (iii) about 50% (w/w) 5-HTP and about 0.0625% (w/w) to about 5% (w/w) carbidopa. In some embodiments, the modified release layer further comprises about 5% (w/w) to about 30% (w/w) of one or more ductile filler based on a total weight of the modified release layer. In some embodiments, the modified release layer further comprises about 0.5% (w/w) to about 3% (w/w) of a lubricant based on a total weight of the modified release layer. In some embodiments, the modified release layer further comprises about 0.01% (w/w) to about 1% (w/w) of an antioxidant based on a total weight of the modified release layer.

In some embodiments, the swelling layer comprises high MW PEO and high viscosity HPMC. In some embodiments, the swelling layer further comprises up to about 5% (w/w) of a lubricant based on a total weight of the swelling layer.

In some embodiments, the swelling layer and the modified release layer have about the same weight. In some embodiments, a total weight of the tablet is about 500 milligrams (mg) to about 2000 mg. In some embodiments, the tablet comprises about 250 mg of 5-HTP and about 0.3125 mg to about 25 mg of carbidopa.

In some embodiments, the modified release layer comprises, based on a total weight of the modified release layer: about 50% (w/w) 5-HTP; about 0.06% (w/w) to about 5.4% (w/w) carbidopa; about 5.7% (w/w) to about 25.1% (w/w) microcrystalline cellulose (MCC); about 5% (w/w) medium or high MW PEO; about 7% (w/w) to about 18% (w/w) medium viscosity HPMC; about 0% (w/w) to about 25% (w/w) high viscosity HPMC; about 0.2% (w/w) butylated hydroxytoluene (BHT), about 0.1% (w/w) colloidal silica; and about 1.5% (w/w) sodium stearyl fumarate (SSF). In some embodiments, the modified release layer comprises, based on a total weight of the modified release layer: about 50% (w/w) 5-HTP; about 0.06% (w/w) to about 5.4% (w/w) carbidopa; about 19.8% (w/w) to about 25.1% (w/w) MCC; about 5% (w/w) medium or high MW PEO; about 18% (w/w) medium viscosity HPMC; about 0.2% (w/w) BHT, about 0.1% (w/w) colloidal silica; and about 1.5% (w/w) SSF.

In some embodiments, the swelling layer swells to at least about 150% of the dry volume of the swelling layer in an aqueous solution. In some embodiments, the tablet remains in the stomach for about 5 hours after oral administration to a human.

In some embodiments, the modified release layer remains chemically stable for at least 70 days when stored at about 15° C. to about 25° C. protected from light. In some embodiments, the modified release layer and the swelling layer remain attached to one another for at least 8 hours during disintegration testing according to USP <701> with use of a disk. In some embodiments, the modified release layer has an acceptance value (AV) of about 15 or less and a relative standard deviation (RSD) of about 3 or less in content uniformity testing according to USP <905>.

In some embodiments, administration of the tablet once or twice daily to a mammalian subject provides a time to achieve a maximum plasma concentration ($T_{Max}$) of 5-HTP that is delayed about 4 hours on average compared to an immediate release dosage form of native 5-HTP. In some embodiments, administration of the tablet once or twice daily to a mammalian subject provides about 1-fold to about 10-fold 5-HTP plasma exposure compared to an immediate release dosage form of native 5-HTP comprising the same weight of 5-HTP as said tablet and wherein said immediate release dosage form of native 5-HTP does not comprise carbidopa. In some embodiments, administration of the tablet once or twice daily to a mammalian subject provides a steady state average 5-HTP plasma level of about 25 nanograms per milliliter (ng/ml) or more.

In some embodiments, administration of the tablet once or twice daily to a mammalian subject provides a steady state average carbidopa plasma level of about 25 ng/ml or less. In some embodiments, administration of the tablet once or twice daily to a mammalian subject provides a steady state average maximum carbidopa plasma level ($C_{Max}$) of about 25 ng/ml or less.

In some embodiments, administration of the tablet once or twice daily to a mammalian subject provides an increased 5-HTP half-life compared to a 5-HTP half-life when native 5-HTP is administered in an immediate release form. In some embodiments, the dosage form is configured to provide a same release rate for 5-HTP and/or a same release rate for carbidopa over a range of carbidopa content from 0.3125 mg to 25 mg when a total combined weight of carbidopa and microcrystalline cellulose is held constant.

Accordingly, it is an object of the presently disclosed subject matter to provide gastroretentive dosage forms or modified/sustained release of 5-HTP and carbidopa. An object of the presently disclosed subject matter having been stated hereinabove, and which is achieved in whole or in part by the presently disclosed subject matter, other objects will become evident as the description proceeds when taken in connection with the accompanying drawings and examples as best described herein below.

BRIEF DESCRIPTION OF THE DRAWINGS

In order that the disclosure may be readily understood and put into practical effect, reference will now be made to examples as illustrated with reference to the accompanying figures. The figures together with the description serve to further illustrate the embodiments of the invention and explain various principles and advantages.

(FIG. 1A) "Fast" bilayer tablet, 250 mg 5-HTP, 0.3125 mg carbidopa. (FIG. 1B) "Fast" bilayer tablet, 250 mg 5-HTP, 25 mg carbidopa. (FIG. 1C) "Slow" bilayer tablet, 250 mg 5-HTP, 0.3125 mg carbidopa. (FIG. 1D) Slow bilayer tablet, 250 mg 5-HTP, 25 mg carbidopa. Conditions: USP III (Reciprocating Cylinder) Dissolution Bath. 250 mL of 0.1 M HCl+ 0.02% disodium EDTA. 37° C.±0.5.

(FIG. 3A) "Fast" bilayer tablet 250 mg 5-HTP 25 mg carbidopa. (FIG. 3B) "Slow" bilayer tablet 250 mg 5-HTP 25 mg carbidopa. (FIG. 3C) "Intermediate" bilayer tablet 250 mg 5-HTP 5 mg carbidopa. Conditions: USP III (Reciprocating Cylinder) Dissolution Bath. 250 mL of 0.1 M HCl+0.02% disodium EDTA. 37° C.±0.5.

FIG. 4: Pair of photographic images showing swelling of the "fast" 5-HTP/low-dose carbidopa gastroretentive tablets. (Image on left) Baseline. (Image on right) At 8 hours. Copley disintegration tester with disk.

(FIGS. 5A-5C) 5-HTP release. (FIGS. 5D-5E) carbidopa release. Carbidopa release at the 0.625 mg carbidopa level could not be assessed as the carbidopa levels were too low to be reliably quantified. Conditions: USP III (Reciprocating Cylinder) Dissolution Bath. 250 mL of 0.1 M HCl+0.02% disodium EDTA. 37° C. f 0.5.

(FIG. 6A) Plasma 5-HTP profiles after single-dose administration of different carbidopa doses of the 5-HTP/low-dose carbidopa gastroretentive tablets compared to 5-HTP immediate release following a HF meal. (FIG. 6B) Plasma 5-HTP profiles after single-dose administration of 250 mg 5-HTP/15 mg carbidopa gastroretentive tablets following a moderate-fat, moderate-calorie (MF) meal compared to after a HF meal, referenced to 5-HTP immediate release after a HF meal. (FIG. 6C) Plasma 5-HTP profiles over 24 h at steady-state, after multiple-dose administration of different carbidopa doses of the 5-HTP/low-dose carbidopa gastroretentive tablets, as modeled by non-parametric superposition; compared to 5-HTP immediate release. (FIG. 6D) $AUC_{0h-12 h}$ plasma 5-HTP levels at steady state, after multiple-dose administration of different carbidopa doses of the 5-HTP/low-dose carbidopa gastroretentive tablets, as modeled by non-parametric superposition; compared to 5-HTP immediate release.

(FIG. 7A) Plasma carbidopa profiles after single-dose administration of different carbidopa doses of the 250 mg 5-HTP/carbidopa gastroretentive tablets. (FIG. 7B) Plasma carbidopa profiles after single-administration of 250 mg 5-HTP/15 mg carbidopa gastroretentive tablets following a moderate-fat, moderate-calorie (MF) meal compared to after a HF meal. (FIG. 7C) Plasma carbidopa levels over 24 h at steady-state, after multiple-dose administration of carbidopa levels at 5 mg and 15 mg of the 5-HTP/low-dose carbidopa gastroretentive tablets, as modeled by non-parametric superposition. (FIG. 7D) $AUC_{0h-12 h}$ plasma carbidopa levels at steady state, after multiple-dose administration of carbidopa dose levels at 5 mg and 15 mg of the 5-HTP/low-dose carbidopa gastroretentive tablets, as modeled by non-parametric superposition.

DETAILED DESCRIPTION

Figure 1B:
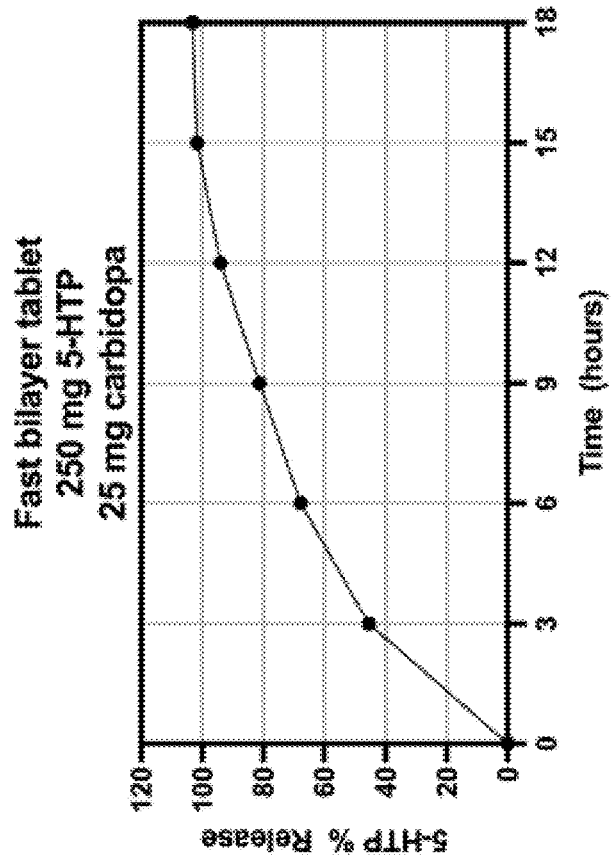
FIGS. 1A-1D: Dissolution testing of 5-HTP/low-dose carbidopa gastroretentive tablets in vitro—5-HTP release from "fast" vs "slow" tablets. 5-HTP release over 18 h.

The presently disclosed subject matter will now be described more fully hereinafter with reference to the accompanying Figures and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

I. DEFINITIONS

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "an agent" or "a polymer" includes a plurality of such agents or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "exposure" refers to the total blood/plasma/serum/bodily levels of a drug integrated over time, usually expressed as area under the curve, either to infinity ($AUC_{0h\text{-}infinity}$), or within a defined time-period (e.g., $AUC_{0h\text{-}12\ h}$). Exposure is often used interchangeably with "levels".

As used herein, a 1-fold change (e.g., a 1-fold increase) refers to an increase of 100% of the baseline value, added to the baseline value, to yield 200% of baseline.

As used herein, the term "treatment" includes references to therapeutic or palliative treatment of patients in need of such treatment, as well as to the prophylactic treatment and/or diagnosis of patients which are susceptible to the relevant disease states to the extent that of these are possible.

The terms "patient" and "patients" include references to mammalian (e.g., human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult, juvenile, and newborn subjects, whether male or female, or not identifying as any specific gender, are intended to be covered.

The term "gastroretentive dosage form" as used herein refer to a dosage form (e.g., an oral dosage form, such as a tablet or capsule) that is retained in the stomach for a time and releases a substantial proportion of the active pharmaceutical ingredient or active pharmaceutical ingredients into the stomach acid and other gastric contents, from where the active pharmaceutical ingredient(s) can travel by bulk flow via the pyloric sphincter into the upper intestine (duodenum, jejunum, ileum) for absorption. After it exits the pylorus, a gastroretentive dosage form can release some of the active pharmaceutical ingredient(s) into the intestine, where additional absorption can occur.

The term "immediate release" refers to a dosage form wherein at least 85% of the active pharmaceutical ingredient (API) content of the dosage form is dissolved within a short time-span, in an aqueous dissolution media of sufficient volume and solubility ensuring the media does not limit the dissolution rate, for which the resulting pharmacokinetic profile does not functionally differ compared to, for example, if the API had been delivered as unformulated powder or in solution as an oral bolus (and provided that the API from the oral bolus does not precipitate when delivered).

The terms "native 5-HTP immediate release", "immediate release native 5-HTP", "immediate release dosage form of native 5-HTP" and the like refer to immediate release administration/formulation of 5-HTP without use of compounds that enhance 5-HTP's bioavailability.

The term "steady state" as used herein refers to pharmacokinetic steady state, either measured in mammalian subjects during repeat dosing over several days, or longer, or extrapolated from single-administration of a compound or compounds in mammals using appropriate mathematical models. At steady state the plasma exposure profile and average level of the compound does not functionally change across different treatment days, provided the compound is administered using the same dose and dosage form and same route and (e.g., oral, intravenous, etc.) mode of administration (e.g., fasted/fed, time of day). Thus, in pharmacokinetics and as used herein, "steady state" can refer to the situation where the overall intake of an active pharmaceutical compound is fairly in dynamic equilibrium with its elimination. The average plasma level of the compound remains about the same from day to day, although there can be intra-day fluctuations related to dosing and elimination. In practice, for most drugs, it typically takes between about 4 and about 6 half-lives to reach steady state after regular dosing is started.

The term "sustained release" refers to drug delivery of an active pharmaceutical ingredient or ingredients that is markedly protracted, such as to producing a delayed $T_{Max}$, a decreased $C_{Max}$, and a prolonged elevated plasma level of the active pharmaceutical ingredient delivered, compared to when said active pharmaceutical compound is delivered as in its immediate release form. "Sustained release" can have synonymous terms, non-limiting examples of which include "slow-release", "extended release", "controlled release", or "modified release".

The term "serotonin reuptake inhibitor" refers to any compound that at plasma exposure levels observed during dosing with therapeutic dosages functionally inhibits the serotonin transporter, i.e., causing an elevation in extracellular serotonin in a tissue or compartment of the body by blocking re-uptake of serotonin into the cell via the serotonin transporter. Non-limiting examples of serotonin reuptake inhibitors include selective serotonin reuptake inhibitors, serotonin-norepinephrine reuptake inhibitors, certain tricyclic antidepressants, vilazodone, vortioxetine, trazodone, nefazodone, methylphenidate, dextromethorphan, amphetamines, and fenfluramine.

The term "matrix", as used herein, denotes its well-known meaning in the pharmaceutical arts, that is, a solid material, optionally having an active ingredient incorporated therein, providing swelling or structural support.

II. GENERAL CONSIDERATIONS

While 5-HTP has moderate bioavailability in in the upper intestine (e.g., ~20%, according to one study), the bioavailability in the colon is low (e.g., ~4%, according to one study) (WO2019245925). Therefore, according to one aspect of the presently disclosed subject matter, a gastroretentive, sustained-release dosage form that delivers 5-HTP to the upper intestine for a prolonged period of time is provided to achieve oral sustained-release delivery of 5-HTP. In a further aspect, a compound, e.g., carbidopa, improving 5-HTP's bioavailability is delivered together with 5-HTP for the gastroretentive, sustained-release dosage form.

Relatively high plasma levels of 5-HTP, i.e., ≥50 ng/ml, appear to be needed for potent pharmacological enhancement of brain serotonin [(Gijsman et al, 2002; Lowe et al, 2006; Meltzer et al, 1997; Sargent et al, 1998; Shenker et al, 1985) and (WO2019245925)], meaning previous 5-HTP treatments have typically involved administration of frequent large doses of 5-HTP. This can present a challenge; and more so as sustained-release formulations often are more limited in the possible dose load due to the presence of release modifying excipients in the dosage form. In previous exploratory studies of 5-HTP in humans, a peripheral decarboxylase inhibitor (PDI) has been co-administered to enhance the bioavailability of 5-HTP (Turner et al, 2006). PDIs inhibit the enzyme aromatic amino acid decarboxylase (AAAD). In the human body, both 5-HTP (the natural immediate serotonin precursor) and L-DOPA (the natural immediate dopamine and norepinephrine precursor) are metabolized by AAAD, to serotonin and dopamine, respectively.

Common PDIs include carbidopa and benserazide. Carbidopa and benserazide are used in regulatorily approved drug products together with L-DOPA to treat Parkinson's Disease. PDIs are usually used in saturating doses, 75-150 mg/day, inhibiting the majority or essentially all of systemic amino acid decarboxylase activity, while leaving brain amino acid decarboxylase activity uninhibited. When previously administered with 5-HTP in the published medical literature, the PDI—usually carbidopa, but sometimes benserazide—has always been administered in one dosage form while the 5-HTP has been administered in a different dosage form. Doses of the PDI given alongside 5-HTP have typically been similar to the PDI doses used in Parkinson's therapy, i.e., 100 mg/day [see e.g., (Magnussen et al, 1982; van Praag, 1982)].

When given with high-dose L-DOPA (400 mg/day), even high-dose PDI (≥100 mg/day) does not prevent a significant fraction of the L-DOPA from being metabolized to dopamine, adrenaline, and noradrenaline in the periphery, thereby preserving the peripheral hormonal and transmitter functions of dopamine, adrenaline, and noradrenaline (Eisenhofer et al, 2014). However, there is evidence that chronic treatment with high-dose PDI to humans not treated with L-DOPA could carry health risks, e.g., by affecting dopamine, adrenaline, and noradrenaline or other transmitter systems and biological processes [discussed in (WO2019148087); and see also (Allen et al, 2009; Garfinkel et al, 1977; Rauws et al, 1982)]. Therefore, it can be desirable to use the lowest possible PDI dose when the PDI is administered chronically to a human or another mammal, in the absence of exogenously administered L-DOPA.

Recently, it was shown that carbidopa is unexpectedly effective in enhancing the bioavailability of 5-HTP under certain conditions, i.e., when carbidopa is administered via a sustained-release mode in temporal and spatial juxtaposition with 5-HTP (U.S. Pat. No. 11,337,963). Without being bound to any one theory, it is believed that to achieve parallel delivery in humans or other mammals using a solid dosage form, such as a sustained-release tablet, the 5-HTP and carbidopa be released at parallel or close to parallel rates from the same dosage form. However, when designing a dosage form for parallel or near parallel release rates of 5-HTP and carbidopa (e.g., low dose carbidopa), there are some particular factors to consider. A first consideration is that drug delivery from most matrices relies to a substantial extent on diffusion. Therefore, parallel delivery of two compounds having different aqueous solubilities from the same matrix is unpredictable and, indeed, is generally not expected. This consideration applies to parallel delivery by sustained-release of 5-HTP and carbidopa, as 5-HTP is sparingly soluble (aqueous solubility~15 mg/ml), whereas carbidopa is slightly soluble (aqueous solubility~1.5 mg/ml). A second consideration, with realizing a sustained-release dosage form of 5-HTP at a medium to high dose (≥200 mg per tablet) with low doses of carbidopa (<10 mg per tablet, <5 mg per tablet, or <1 mg per tablet), is to attain content uniformity for the low dose of carbidopa. For example, given the need for release modifying excipients, a drug delivery layer total weight can be approximately twice the weight of the active pharmaceutical ingredients. When formulating low doses of carbidopa, in many cases that would mean that the carbidopa content be about 1% w/w or less of total drug delivery layer weight. A third consideration is that the stability of carbidopa in the presence of 5-HTP, and vice versa, generally cannot be assumed, as no validated/regulatorily approved pharmaceutical product containing 5-HTP and carbidopa is currently available. A fourth consideration, when formulating solid dosage forms holding large API levels, e.g., as for 5-HTP, is that different dose levels/dose strength can involve different distinct formulations to achieve approximately similar drug delivery profiles. Matching the delivery profiles of two distinct formulations in vitro and in vivo can be challenging, cumbersome, expensive, and not always possible. Further, different formulations for the same drug product at different dose strengths can encumber drug development and drug manufacturing.

An additional consideration with the formulation compositions of two or more active pharmaceutical ingredients within the same dosage form is to ensure stability of the active pharmaceutical ingredients, together, as well as together with the selected excipients. This can be a particular issue for carbidopa, which can be chemically unstable under some conditions, e.g., in solution or suspension (Donnelly, 2016).

Previous studies using different dose combinations of 5-HTP and carbidopa, in separate dosage forms for 5-HTP and for carbidopa, to obtain varying plasma levels of 5-HTP in the human body, have been published. These studies used fixed daily doses of carbidopa, typically 100 mg per day to 300 mg per day with varying doses of 5-HTP, 250 mg per day to 2800 mg per day [see e.g., (Magnussen et al, 1982; van Hiele, 1980; van Praag, 1982)].

As described hereinabove, both 5-HTP and L-DOPA are metabolized in the body by AAAD. The PDI carbidopa is used clinically to enhance the systemic plasma exposure of L-DOPA. Sustained-release formulations of L-DOPA and carbidopa are known in the art, typically employing per tablet doses of carbidopa of ≥25 mg and L-DOPA:carbidopa ratios of 4:1. For example, L-DOPA/carbidopa tablets sold under the tradename SINEMET® CR (Organon & Co., Jersey City, N.J., United States of America) are supplied as a conventional (non-gastroretentive) sustained-release tablet containing either 50 mg of carbidopa and 200 mg of L-DOPA, or 25 mg of carbidopa and 100 mg of L-DOPA. The starting dose of SINEMET® CR is 200 mg/50 mg L-DOPA/carbidopa, twice daily, for a total daily starting dose of 400 mg/100 mg L-DOPA/carbidopa. Similarly, gastroretentive tablets of L-DOPA/carbidopa have been described, containing 200 mg L-DOPA and of 50 mg carbidopa, for twice daily dosing, for a total daily dose of 400 mg L-DOPA and of 100 mg carbidopa (U.S. Pat. No. 9,161,911).

III. GASTRORETENTIVE, SUSTAINED-RELEASE TABLET DOSAGE FORMS OF 5-HTP

In some embodiments, the presently disclosed subject matter provides a gastroretentive, dosage form for 5-HTP and carbidopa (e.g., low-dose carbidopa). In some embodiments, the gastroretentive dosage form is a gastroretentive, sustained release dosage form for 5-HTP and carbidopa. In some embodiments, the dosage form is a tablet.

In some embodiments, the presently disclosed gastroretentive dosage form (e.g., tablet) is configured to provide 5-HTP plasma levels that are elevated (i.e., maintained above baseline levels) most of the day when the dosage form is administered to a mammal, such as a human. In some embodiments, the dosage form is configured to provide elevated 5-HTP plasma levels most of the day with twice-daily dosing of the dosage form to a mammal. In some embodiments, the dosage form is configured to provide elevated 5-HTP plasma levels with once-daily dosing of the dosage form to a mammal. In some embodiments, the dosage form is configured to provide elevated 5-HTP plasma levels when the dosage form is provided for three or more daily dosages to a mammal. In some embodiments the presently disclosed dosage form is configured to provide 5-HTP plasma levels that are elevated above baseline by about 25 ng/ml, about 50 mg/ml, about 75 ng/ml, or about 100 ng/ml most of the day (e.g., at least about 14, about 16, about 18, about 20, or about 22 hours of each 24-hour period) or all of the day. In some embodiments the 5-HTP plasma exposure after administration of the presently disclosed dosage form (e.g., once or twice daily) is elevated from about 1-fold to about 10-fold (e.g., about 1-fold, 2-fold, 3-fold, 4-fold, 5-fold, 6-fold, 7-fold, 8-fold, 9-fold, or about 10-fold) compared to administration of native 5-HTP immediate release at the same 5-HTP dose (e.g., to an immediate release dosage form of native 5-HTP that does not contain carbidopa).

In some embodiments, the presently disclosed gastroretentive dosage form (e.g., tablet) is configured (e.g., is further configured) to delay the time it takes to achieve maximum plasma concentration ($T_{Max}$) of 5-HTP (e.g., with once or twice daily dosing), relative to administration of native 5-HTP immediate release, by about 1-fold to about 10-fold. In some embodiments, $T_{Max}$ is delayed about 1-fold to about 5-fold. In some embodiments, $T_{Max}$ is delayed about 4-fold. In some embodiments, $T_{Max}$ is delayed to about 3 hours to about 10 hours (e.g., about 3 hours, about 3.5 hours, about 4.0 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, or about 10 hours) compared to administration of native 5-HTP immediate release. In some embodiments, $T_{Max}$ is delayed about 2 hours to about 6 hours or about 3 hours to about 5 hours. In some embodiments, $T_{Max}$ is delayed to about 4 hours.

In some embodiments, the presently disclosed gastroretentive dosage form comprises, consists essentially or, or consists of a tablet (e.g., a gastroretentive, sustained release bilayer tablet) of about 500 mg to about 2000 mg total weight. In some embodiments, the total weight of the tablet is between about 1000 mg and about 2000 mg. In some embodiments, the total weight of the tablet is between about 800 mg to about 1200 mg. In some embodiments, the total weight of the tablet is about 1000 mg to about 1200 mg. In some embodiments, the total weight of the tablet is about 1000 mg. In some embodiments, the total weight of the tablet is between about 1200 mg and about 1600 mg. In some embodiments, the total weight of the tablet is about 500 mg to about 1000 mg. In some embodiments, the total weight of the tablet is about 700 mg to about 850 mg.

In some embodiments the tablet comprises a swelling layer and a modified release layer. In some embodiments, the tablet is a bilayer tablet. In some embodiments, the swelling layer comprises one or more hydrophilic polymers (e.g., one or more hydrophilic polymers that are swellable in the presence of gastric fluid). In some embodiments, the modified release layer comprises 5-HTP and carbidopa (e.g., low dose carbidopa). In some embodiments, the swelling layer does not contain any 5-HTP or carbidopa. In some embodiments, only the modified release layer contains 5-HTP and carbidopa. In some embodiments, the modified release layer comprises 5-HTP, carbidopa, and one or more polymers that can provide modified release of the 5-HTP and/or carbidopa. In some embodiments the swelling layer imparts most of the volume (e.g., about 60%, 70%, 80%, 90% or more) of the total volume of the tablet when the tablet is exposed to an aqueous medium (e.g., after administration of the tablet to a mammal or exposure of the tablet to gastric fluid or another aqueous medium). In some embodiments, the swelling layer and modified release layer have approximately equal sizes (e.g., approximately equal weights) when the tablet is dry. In some embodiments, the sizes (e.g., weights) of the layers differ when the tablet is dry.

In some embodiments, the presently disclosed gastroretentive dosage form is provided as an oval or a rectangular tablet. In some embodiments said tablet has beveled or rounded corners. In some embodiments, the tablet is about twice as long as it is wide prior to swelling. In some embodiments, prior to swelling, the tablet is about 19 mm in length, about 9.5 mm in width, and about 7 mm in depth.

In some embodiments, the dose per gastroretentive dosage form (e.g., tablet) is about 250 mg 5-HTP. Thus, in some embodiments, the modified release layer comprises about 250 mg 5-HTP. In some embodiments, the modified release layer also contains carbidopa. In some embodiments, the per dosage form dose of carbidopa is about 0.3125 mg to about 25 mg. Thus, in some embodiments, the modified release layer comprises about 0.3125 mg to about 25 mg of carbidopa. In some embodiments, the dose of carbidopa is about 0.3125 mg, about 0.625 mg, about 2.5 mg, about 5 mg, about 10 mg, about 15 mg, about 20 mg, or about 25 mg.

In some embodiments, the presently disclosed gastroretentive dosage form (e.g., tablet) is configured such that the release of 5-HTP and carbidopa from the modified release layer is essentially in parallel. For example, in some embodiments, the dosage form is configured such that the time period (i.e., the amount of time) for a given percentage of the total weight of the 5-HTP in the dosage form to release from the dosage form (e.g., as measured via dissolution testing in an aqueous medium) is within about 2 hours (e.g., within about 2 hours, about 1.5 hours, about 1 hour, or about 30 minutes) of the time period for a corresponding percentage of the total weight of the carbidopa in the dosage form to release from the dosage form under the same conditions. For instance, the dosage form can be configured such that the time period for release of 80% of the weight (in dissolution testing: T=80%, T=80%, or T80%) of one of the 5-HTP and the carbidopa (i.e., the time it takes for 80% of the weight of the 5-HTP or carbidopa to be released from the dosage form after the dosage form is introduced into an aqueous medium) is within about 2 hours of the T=80% of the other. In some embodiments, the time-period for release of 50% of the weight (dissolution T=50%, T=50%, or T50%) of the 5-HTP or the carbidopa is within about 2 hours of the T=50% of the other. In some embodiments, T=50% and T=80% for 5-HTP (T=50%$_{(5-HTP)}$ and T=80%$_{(5-HTP)}$) are within about 2 hours of the T=50% and T=80% for carbidopa (T=50%$_{(carbidopa)}$ and T=80%$_{(carbidopa)}$), respectively. In some embodiments, the T=80% and T=50% are measured via dissolution testing using a U.S. Pharmacopeia (USP) Apparatus III (Reciprocating Cylinder) at 37° C. in a suitable volume of a suitable aqueous medium (e.g., 250 mL of 0.1 molar (M) hydrochloric acid (HCl) and 0.02% disodium ethylenediaminetetraacetic acid (EDTA)). Thus, in some embodiments, the T=80% of the 5-HTP (T=80%$_{(5-HTP)}$) is no more than 2 hours greater than or 2 hours less than T=80% of the carbidopa (T=80%$_{(carbidopa)}$) when T=80% (5-THP) and T=80% (carbidopa) are measured via dissolution testing using USP Apparatus III (Reciprocating Cylinder) in 250 mL of 0.1 molar (M) hydrochloric acid (HCl) and 0.02% disodium ethylenediaminetetraacetic acid (EDTA)). In some embodiments, the dissolution T=50% and T=80% for 5-HTP are within about 1 hour of the T=50% and T=80% for carbidopa, respectively. In some embodiments, the dissolution T=50% and T=80% for 5-HTP are within about 0.5 hours of the T=50% and T=80% for carbidopa, respectively.

In some embodiments, the time-period for 80% by weight of one or both of the 5-HTP and the carbidopa to release from the dosage form (i.e., T=80%$_{(5-HTP)}$, T=80%$_{(carbidopa)}$, or both T=80%$_{(5-HTP)}$ and T=80%$_{(carbidopa)}$) are about 4 hours to about 15 hours. In some embodiments, T=80%$_{(5-HTP)}$ and/or T=80%$_{(carbidopa)}$ is about 5 hours to about 12 hours. In some embodiments, T=80%$_{(5-HTP)}$ and T=80%$_{(carbidopa)}$ are each about 5 hours to about 12 hours (e.g., about 5 hours, about 5.5 hours, about 6 hours, about 6.6 hours, about 7 hours, about 7.5 hours, about 8 hours, about 8.5 hours, about 9 hours, about 9.5 hours, about 10 hours, about 10.5 hours, about 11 hours, about 11.5 hours, or about 12 hours).

As described above, in some embodiments, the swelling layer of the gastroretentive dosage form comprises one or more hydrophilic polymers that swell in an aqueous medium (e.g., gastric fluid). In this regard, with increasing molecular weight, the number of inter-polymeric entanglements in a hydrophilic polymer can increase. These entanglements can act like physical crosslinks, forming a matrix. When water is imbibed into the matrix, the matrix can form a gel of a volume larger than the swelling layer dry volume.

In the context of the use of hydrophilic polymers for modified release of APIs (e.g., in the modified release layer of the presently disclosed tablet), high molecular weight can cause more polymeric entanglement and slow the rate of polymeric dissolution in an aqueous medium, so that erosion is typically slower than the desired time for drug delivery for APIs of low aqueous solubility. For lower molecular weight hydrophilic polymers, erosion can predominate, and release can be rapid. For intermediate molecular weight hydrophilic polymers, erosion can be the primary mechanism of release for aqueous sparingly soluble or insoluble APIs and provide enough swollen gel for diffusion of more soluble APIs.

Polyethylene oxides are a representative class of hydrophilic polymer. Thus, in some embodiments, the swelling and/or modified release layer of the presently disclosed gastroretentive dosage form (e.g., tablet) comprises one or more polyethylene oxide (PEO) polymer, such as those available under the tradename POLYOX® (Dow Chemical Company, Midland, Mich., United States of America). In some embodiments, the swelling layer can include one or more PEO polymers wherein each of the PEO polymers, if more than one, can have a different molecular weight (MW). In some embodiments, the swelling layer comprises a high MW PEO.

By "high molecular weight PEO" or "high MW PEO" as used herein is meant PEO with an average molecular weight (e.g., as measured via a suitable method, such as by rheological measurements) of about 4,000,000 or more (e.g., about 4,000,000 to about 8,000,000). Exemplary high MW PEOs include, but are not limited to, POLYOX® WSR 301 (which can also be referred to as PEO WSR 301), which has an average MW of about 4,000,000; POLYOX® WSR coagulant (which can also be referred to as POLYOX® Coag), which has an average MW of about 5,000,000; POLYOX® WSR 303, which has an average MW of about 7,000,000; and PEO 308, which has an average MW of about 8,000,000. By "medium molecular weight PEO" or "medium MW PEO" as used herein is meant PEO with an average MW of about 900,000 to about 4,000,000. Exemplary medium MW PEOs include, but are not limited to, PEO WSR 1105, which has an average MW of about 900,000; PEO WSR N12K, which has an average MW of about 1,000,000; PEO WSR N60K, which has an average MW of about 2,000,000; and PEO WSR 301. Thus, PEO WSR 301 can be considered as a medium and/or high MW PEO as used herein. Exemplary "low molecular weight PEO" or low "MW PEO" as used herein include PEO with an average MW of about 900,000 or less, such as, but not limited to, PEO WSR N10, which has an average MW of about 100,000; and PEO WSR 1105, which has an average MW of about 900,000. PEO WSR 1105 can thus be considered as a low and/or medium MW PEO according to the presently disclosed subject matter.

Alkyl-substituted celluloses with substituted alkyl groups of 1 to 3 carbons are a representative class of hydrophilic polymers. Representative alkyl-substituted cellulosic polymers for swelling are hydroxyethylcellulose (HEC), hydroxypropylmethylcellulose (HPMC or Hypromellose), and carboxymethylcellulose (CMC). Particular representative alkyl-substituted celluloses include HPMC and HEC. HPMC can be characterized by the viscosity of a 2% aqueous solution at 20° C., and HEC (NATROSOL™) can be characterized by the viscosity of a 1% solution at 25° C. with a typical Brookfield viscosity of 3400-5000 MPa-s. For HPMC it is convenient to define a "low" viscosity, "medium" viscosity, and "high" viscosity range. "Low" viscosity HPMC is defined as about 2 MPa-s to 500 MPa-s. Examples of low viscosity HPMC are METHOCEL™ K3LV with a viscosity of 2.4 to 3.6 MPa-s, K100LV with a viscosity of 100-120 MPa-s, and E5-LV with a viscosity of 7 to 12 MPa-s. "Medium" viscosity HPMC is defined as between about 550 MPa-s and about 30,000 MPa-s. Particular examples of medium viscosity HPMC are METHOCEL™ K4M with a viscosity of 2,663 MPa-s to 4,970 MPa-s, K15M with a viscosity of 13,275 MPa-s to 24,780 MPa-s, and E4M with a viscosity of 2,663 MPa-s to 4,970 MPa-s. "High" viscosity HPMC is defined as between about 30,000 MPa-s and about 200,000 MPa-s. An example of high viscosity HPMC is METHOCEL™ K100M with a viscosity of 75,000 MPa-s to 140,000 MPa-s.

In some embodiments the swelling layer of the gastroretentive dosage form (e.g., tablet) comprises a high viscosity HPMC. Various HPMCs are available under the tradenames BENECEL™ from Ashland Inc. (Wilmington, Del., United States of America) and METHOCEL™ (Dupont de Nemours, Inc., Wilmington, Del., United States of America).

An example of high viscosity HPMC is HPMC K100M, where a 2% aqueous solution at 20° C. has a viscosity of 75,000 MPa-s to 140,000 MPa-s and the K indicates a methoxy substitution of 19.0%-24.0%. A medium viscosity HPMC used as a binder for granulation and erosional drug release is HPMC K4M where a 2% aqueous solution at 20° C. has a viscosity of 2,663 MPa-s to 4,970 MPa-s and the K indicates a methoxy substitution of 19.0%-24.0%. HPMC K100 LVCR is an example of a low viscosity HPMC that is used for sustained release and where a 2% aqueous solution at 20° C. has a viscosity of 80 MPa-s to 120 MPa-s and the K indicates a methoxy substitution of 19.0-24.0%. In some embodiments, the swelling layer comprises a high viscosity hydroxyethyl cellulose (HEC), such as that sold under the tradename NATROSOL™ 250 HX Pharm from Ashland Inc. (Wilmington, Del., United States of America) with a viscosity of 1,500 MPa-s to 2,500 mPa-s; NATROSOL™ 250 HHX Pharm from Ashland Inc. (Wilmington, Del., United States of America) with a viscosity of a 1% aqueous solution at 25° C. of 3,500 MPa-s to 5,500 mPa-s; or CELLOSIZE™ 15000H from Dow Chemical Company (Midland, Mich., United States of America), where a 1% aqueous solution has a viscosity of 1,100 cP to 1,500 cP.

In some embodiments, the swelling layer of the gastroretentive, sustained-release dosage form (e.g., tablet) comprises a high molecular weight hydrophilic polymer and a gas generating agent, such as sodium bicarbonate, calcium carbonate, or magnesium carbonate; optionally an organic acid, such as citric acid, fumaric acid, maleic acid, or another common organic acid suitable as a pharmaceutical excipient.

In some embodiments, the swelling layer of the gastroretentive dosage form (e.g., tablet) is made from a blend of polymers that comprises approximately equal parts (by weight or volume) high MW PEO and high viscosity HPMC. In some embodiments, the swelling layer comprises a weight ratio of high MW PEO:high viscosity HPMC of about 1:1. In some embodiments, the swelling layer comprises high MW PEO. In some embodiments, the swelling layer comprises up to about 50% (w/w) high MW PEO and up to about 50% (w/w) high viscosity HPMC (e.g., based on the total weight of the swelling layer).

In some embodiments, the swelling layer further comprises a lubricant. In some embodiments, the lubricant is present in less than about 5%, about 3%, about 1%, or about 0.5% (w/w) (i.e., based on the total weight of the swelling layer). In some embodiments, the lubricant comprises sodium stearyl fumarate, glyceryl behenate, stearic acid, magnesium stearate, or a mixture thereof. In some embodiments, the lubricant comprises or consists of sodium stearyl fumarate (SSF). In some embodiments, the swelling layer further comprises a glidant. In some embodiments, the swelling layer further comprises an antioxidant. Suitable antioxidants include, but are not limited to, butylated hydroxytoluene (BHT), butylated hydroxyanisole, tocopherol, tocopherol acetate, ascorbic acid, sodium sulfite, sodium metabisulfite, and mixtures thereof. In some embodiments, the antioxidant is BHT.

In some embodiments, the swelling layer of the gastroretentive dosage form (e.g., tablet) swells when imbibing water, gastric fluid, or another aqueous media to about 200% or more than the dry volume. In some embodiments the swelling layer swells to about 150% of the dry volume. In some embodiments the swelling layer is still essentially intact (e.g., is in one mass with substantially no disintegration) after about 8 hours or longer during disintegration testing according to USP <701> with use of a disk.

In some embodiments, the carbidopa of the gastroretentive dosage form (e.g., tablet) is delivered together with 5-HTP from the same modified release layer (i.e., the modified release layer of a bilayer tablet). In some embodiments, the swelling layer attaches/adheres to the modified release layer without any binder or binding layer between the modified release layer and the swelling layer. In some embodiments, the modified release layer and the swelling layer remain attached to one another for at least 8 hours during disintegration testing according to USP <701> with use of a disk. In some embodiments, the modified release layer comprises PEO, e.g., to enhance adhesion between the modified and swelling layers. In some embodiments, the PEO is present in the modified release layer in about 1% (w/w) to about 10% (w/w) based on the total weight of the modified release layer. In some embodiments, the modified release layer remains attached directly or indirectly to the swelling layer through substantially the entire drug release period.

In some embodiments, the modified release layer of the gastroretentive dosage form (e.g., tablet) comprises about 50% (w/w) 5-HTP based on the total weight of the modified release layer. In some embodiments, the modified release layer comprises about 0.0625% (w/w) to about 5% (w/w) of carbidopa based on the total weight of the modified release layer. In some embodiments, the modified release layer comprises about 50% (w/w) 5-HTP and about 0.0625% (w/w) to about 5% (w/w) carbidopa based on the total weight of the modified release layer. Thus, in some embodiments, such as when the dosage form is a bilayer tablet that has a total weight of about 1000 mg and the modified release layer and the swelling layer have about the same weight, the tablet (e.g., the modified release layer) comprises about 250 mg of 5-HTP. In some embodiments, the tablet (e.g., the modified release layer) comprises about 0.3125 mg to about 25 mg carbidopa. In some embodiments, the tablet (e.g., the modified release layer) comprises about 250 mg 5-HTP and about 0.3125 mg to about 25 mg carbidopa.

In some embodiments, the modified release layer comprises one or more one or more hydrophilic polymers selected from a low viscosity HPMC, a medium viscosity HPMC, a high viscosity HPMC, a low MW PEO, a medium MW PEO, a high MW PEO, and a high viscosity hydroxyethyl cellulose. The modified release layer can comprise a single hydrophilic polymer or a combination of two, three or more a low viscosity HPMC, a medium viscosity HPMC, a high viscosity HPMC, a low MW PEO, a medium MW PEO, a high MW PEO, and a high viscosity hydroxyethyl cellulose. The modified release layer can also comprise multiple polymers of the same type (e.g., two or more medium viscosity HPMC). In some embodiments, the modified release layer comprises about 14% (w/w) to about 37% (w/w) (e.g., about 14% (w/w), 15% (w/w), 16% (w/w), 17% (w/w), 18% (w/w), 19% (w/w), 20% (w/w), 21% (w/w), 22% (w/w), 23% (w/w), 24% (w/w), 25% (w/w), 26% (w/w), 27% (w/w), 28% (w/w), 29% (w/w), 30% (w/w), 31% (w/w), 32% (w/w), 33% (w/w), 34% (w/w), 35% (w/w), 36% (w/w), or about 37% (w/w)) of the one or more hydrophilic polymers (based on a total weight of the modified release layer). For example, in some embodiments, the release rate of 5-HTP and carbidopa in the modified release layer of the gastroretentive tablet formulation is controlled by the level of medium viscosity HPMC, such as HPMC K4M. In some embodiments, a mixture (i.e., a blend) of medium and high viscosity hydroxypropyl methylcellulose, such as HPMC K100M, controls the release rate. Thus, in some embodiments, HPMC is present in the modified release layer in about 10% to about 35% (w/w) based on the total weight of the modified release layer. In some embodiments, the modified release layer comprises about 15% (w/w) to about 35% (w/w) HPMC. In some embodiments, medium to high MW PEO in the modified release layer controls the release of the drug. Accordingly, in some embodiments, the modified release layer comprises medium and/or high MW PEO. In some embodiments, the modified release layer comprises about 5% (w/w) of a medium MW PEO and/or a high MW PEO and about 13% (w/w) to about 32% (w/w) of a low viscosity HMPC, a medium viscosity HPMC, or a mixture (i.e., a blend) of medium viscosity HPMC and high viscosity HPMC.

In some embodiments, the modified release layer of the gastroretentive dosage form (e.g., tablet) comprises a filler. In some embodiments, the filler comprises or consists of microcrystalline cellulose (MCC) or another ductile (i.e., non-brittle) filler, such as, but not limited to, calcium sulfate, cellulose, dicalcium phosphate, kaolin, lactose, mannitol, sodium chloride, sorbitol, starch, sucrose, or mixtures thereof. In some embodiments, the filler can improve tablet properties (e.g., hardness) in addition to maintaining the larger tablet size while having a neutral effect on drug release. In some embodiments, the modified release layer comprises about 5% (w/w) to about 30% (w/w) MCC based on the total weight of the modified release layer (e.g., about 5% (w/w), 10% (w/w), 15% (w/w) 20% (w/w), 25% (w/w), or about 30% (w/w) MCC). In some embodiments, the modified release layer comprises about 20% (w/w) MCC based on the total weight of the modified release layer. In some embodiments, the modified release layer comprises about 25% (w/w) MCC based on the total weight of the modified release layer.

In some embodiments, the modified release layer of the gastroretentive sustained-release dosage form further comprises a lubricant. In some embodiments, the lubricant comprises or consists of SSF. In some embodiments, the modified release layer comprises about 0.5% (w/w) to about 3% (w/w) of a lubricant (e.g., SSF) based on the total weight of the modified release layer. Other exemplary lubricants include, but are not limited to, glyceryl behenate, stearic acid, or magnesium stearate.

In some embodiments, the modified release layer of the gastroretentive sustained-release tablet formulation further comprises an antioxidant. In some embodiments, the antioxidant comprises or consists of butylated hydroxytoluene (BHT). In some embodiments, the modified release layer comprises about 0.05% (w/w) to about 1% (w/w) based on the total weight of the modified release layer. Other exemplary antioxidants include, but are not limited to, butylated hydroxyanisole, tocopherol, tocopherol acetate, ascorbic acid, sodium sulfite, sodium metabisulfite, and others listed in the Handbook of Pharmaceutical Excipients.

In some embodiments, the presently disclosed subject matter provides a gastroretentive bilayer tablet comprising a swelling layer and a modified release layer, wherein the modified release layer comprises, based on a total weight of the modified release layer: about 50% (w/w) 5-HTP; about 0.06% (w/w) to about 5.4% (w/w) carbidopa; about 5.7% (w/w) to about 25.1% (w/w) MCC, about 5% (w/w) medium or high MW PEO; about 7% (w/w) to about 18% (w/w) medium viscosity HPMC; about 0% (w/w) to about 25% (w/w) high viscosity HPMC; about 0.2% (w/w) BHT, about 0.1% (w/w) colloidal silica; and about 1.5% (w/w) SSF. In some embodiments, the modified release layer comprises, based on a total weight of the modified release layer: about 50% (w/w) 5-HTP; about 0.06% (w/w) to about 5.4% (w/w) carbidopa; about 19.8% (w/w) to about 25.1% (w/w) MCC; about 5% (w/w) medium or high MW PEO; about 18% (w/w) medium viscosity HPMC; about 0.2% (w/w) BHT, about 0.1% (w/w) colloidal silica; and about 1.5% (w/w) SSF. In some embodiments, the swelling layer comprises, based on a total weight of the swelling layer, about 49.55 (w/w) high MW PEO, about 49.5% (w/w) high viscosity HPMC and about 1% (w/w) of a lubricant (e.g., SSF). In some embodiments, the weight of the modified release layer and the swelling layer are approximately the same. In some embodiments, the weight of tablet is about 800 mg to about 1200 mg. In some embodiments, the weight of the table is about 1000 mg. Thus, in some embodiments, the weight of each of the swelling layer and the modified release layer is about 500 mg.

In some embodiments, the gastroretentive dosage form (e.g., tablet) is coated to enhance swallowing. In some embodiments, the coating has no or minimal functional effect on the swelling and drug delivery of the tablet. In some embodiments, the coating adds a color. In some embodiments, the coating is taste-masking.

Tablet hardness for the gastroretentive tablet is, in some embodiments, about 22 kilopond (Kp) to about 28 Kp. In some embodiments, the tablet hardness is about 24 Kp to about 26 Kp. In some embodiments, the tablet hardness is about 25 Kp.

Methods for determining disintegration and content uniformity are known in the art, including the methods described in U.S. Pharmacopeia ("USP") <905> ("Uniformity of Dosage Units" (2011)) and USP <701> ("Disintegration" (2016)), each of which is incorporated herein by reference for all purposes.

In some embodiments, the content uniformity of 5-HTP and of carbidopa in gastroretentive dosage form (e.g., tablet) meets the requirements of USP <905> ("Uniformity of Dosage Units", 2011). In some embodiments, the modified release layer has an acceptance value (AV, calculated as per USP <905>) of about 15 or less in content uniformity testing. In some embodiments, the modified release layer has a relative standard deviation (RSD) of about 3% or less in content uniformity testing. In some embodiments, the modified release layer has an AV of about 15 or less and an RSD of about 3% or less in content uniformity testing. In some embodiments, the modified release layer remains stable (e.g., physically and/or chemically stable) for at least 70 days when stored at 15° C. to about 25° C. and protected from light. In some embodiments, the gastroretentive dosage form (e.g., tablet) remains physically and chemically stable for at least 70 days when stored at 15° C. to about 25° C. and protected from light.

While the time the gastroretentive dosage form remains in the stomach can vary by individual, in some embodiments, the gastroretentive dosage form (e.g., tablet) swells in the stomach (e.g., in the fed state, i.e., when the dosage form is orally administered to a human at the same time or within about 15 minutes after a meal) and is retained in the stomach, on average across a group of subjects, as assessed by scintigraphy, for about 4 hours to about 6 hours. In some embodiments, the dosage form is retained in the stomach for about 5 hours.

In some embodiments, delivery rate of 5-HTP from the gastroretentive sustained-release tablet formulation is unaffected by the level of carbidopa. For example, the dose of carbidopa in the modified release layer can be adjusted (e.g., from about 0.3125 mg to about 25 mg) without affecting the release rate of the 5'-HTP by adjusting the level of ductile filler (e.g., MCC) such that the total combined weight of the carbidopa and ductile filler remains constants. For example, at higher carbidopa content, the modified release layer can include less ductile filler, while at lower carbidopa content, the modified release layer can include more ductile filler. Stated another way, the dosage form is configured to maintain the same 5-THP release rate over a range of different carbidopa content values by inversely adjusting the amount of ductile filler based on the carbidopa content. In some embodiments, the dosage form is configured to provide a same release rate for 5-HTP and/or a same release rate for carbidopa over a range of carbidopa content from 0.3125 mg to 25 mg when a total combined weight of carbidopa and microcrystalline cellulose is held constant. Thus, in some embodiments, the T=80% for carbidopa and/or 5-HTP is the same value whether the dosage form contains 0.3125 mg carbidopa or 25 mg carbidopa or any value therebetween.

In some embodiments, the 5-HTP dose per gastroretentive dosage form (e.g., tablet) is fixed, while the carbidopa dose per tablet is varied, in order to obtain varying plasma 5-HTP levels fitting the needs of the therapeutic scenario. In some embodiments, the 5-HTP dose is fixed at about 250 mg per tablet, while the carbidopa dose is varied from about 0.3125 mg to about 25 mg. In some embodiments, the fixed dose of 5-HTP is lower than 250 mg; in some embodiments, the fixed dose of 5-HTP is higher than 250 mg. In some embodiments, the fixed per tablet 5-HTP dose is about 25 mg, about 50 mg, about 100 mg, about 200 mg, about 300 mg, about 400 mg, or about 500 mg, while the carbidopa dose per tablet is varied.

In some embodiments, the carbidopa dose per gastroretentive dosage form (e.g., tablet) enhances 5-HTP plasma exposure from a given fixed dose of 5-HTP by about 1-fold to about 10-fold compared to the plasma exposure resulting from the same dose of native 5-HTP immediate release form. In some embodiments, the carbidopa dose enhances 5-HTP plasma exposure from a given fixed dose of 5-HTP by about 0.5-fold to about 3-fold compared to the plasma exposure resulting from the same dose of native 5-HTP immediate release form. In some embodiments, the carbidopa dose enhances 5-HTP plasma exposure from a given fixed dose of 5-HTP by about 3-fold to about 10-fold compared to the plasma exposure resulting from the same dose of 5-HTP administered in its native 5-HTP immediate release form.

In some embodiments, the dose ranges of carbidopa used with the fixed 5-HTP dose in the gastroretentive dosage form (e.g., tablet) enhance 5-HTP plasma exposure about 1-fold to about 10-fold compared to the plasma exposure resulting from the same dose of 5-HTP administered in its native 5-HTP immediate release form, while carbidopa plasma levels reach average $C_{Max}$ values at steady state of ≤about 5 ng/ml. In some embodiments, the dose ranges of carbidopa used with the fixed 5-HTP dose enhance 5-HTP plasma exposure about 1-fold to about 10-fold, while carbidopa plasma levels reach averages at steady state of ≤about 5 ng/ml. In some embodiments, the dose ranges of carbidopa used with the fixed 5-HTP dose in the gastroretentive dosage form (e.g., tablet) enhance 5-HTP plasma exposure about 1-fold to about 10-fold compared to the plasma exposure resulting from the same dose of 5-HTP administered in its native 5-HTP immediate release form, while carbidopa plasma levels reach average $C_{Max}$ values at steady state of ≤about 10 ng/ml. In some embodiments, the dose ranges of carbidopa used with the fixed 5-HTP dose enhance 5-HTP plasma exposure about 1-fold to about 10-fold compared to the plasma exposure resulting from the same dose of 5-HTP administered in its native 5-HTP immediate release form, while carbidopa plasma levels reach averages at steady state of ≤about 10 ng/ml.

In some embodiments, the dose ranges of carbidopa used with the fixed 5-HTP dose in the gastroretentive dosage form (e.g., tablet) enhance 5-HTP plasma exposure about 1-fold to about 10-fold, compared to the plasma exposure resulting from the same dose of 5-HTP administered in its native 5-HTP immediate release form, while carbidopa plasma levels reach average $C_{Max}$ values at steady state of ≤about 15 ng/ml. In some embodiments, the dose ranges of carbidopa used with the fixed 5-HTP dose enhance 5-HTP plasma exposure about 1-fold to about 10-fold compared to the plasma exposure resulting from the same dose of 5-HTP administered in its native 5-HTP immediate release form, while carbidopa plasma levels reach averages at steady state of ≤about 15 ng/ml.

In some embodiments, the dose ranges of carbidopa used with the fixed 5-HTP dose in the gastroretentive dosage form (e.g., tablet) enhance 5-HTP plasma exposure about 1-fold to about 10-fold, compared to the plasma exposure resulting from the same dose of 5-HTP administered in its native 5-HTP immediate release form, while carbidopa plasma levels reach average $C_{Max}$ values at steady state of ≤about 20 ng/ml. In some embodiments, the dose ranges of carbidopa used with the fixed 5-HTP dose enhance 5-HTP plasma exposure about 1-fold to about 10-fold, compared to the plasma exposure resulting from the same dose of 5-HTP administered in its native 5-HTP immediate release form, while carbidopa plasma levels reach averages at steady state of ≤about 20 ng/ml.

In some embodiments, the dose ranges of carbidopa used with the fixed 5-HTP dose in the gastroretentive dosage form (e.g., tablet) enhance 5-HTP plasma exposure about 1-fold to about 10-fold, compared to the plasma exposure resulting from the same dose of 5-HTP administered in its native 5-HTP immediate release form, while carbidopa plasma levels reach average $C_{Max}$ values at steady state of ≤about 20 ng/ml. In some embodiments, the dose ranges of carbidopa used with the fixed 5-HTP dose enhance 5-HTP plasma exposure about 1-fold to about 10-fold, compared to the plasma exposure resulting from the same dose of 5-HTP administered in its native 5-HTP immediate release form, while carbidopa plasma levels reach averages at steady state of ≤about 25 ng/ml.

In some embodiments, the 5-HTP plasma exposure produced by the gastroretentive dosage form (e.g., tablet) increases, as compared 5-HTP in its native immediate release form, as a function of higher carbidopa doses in the modified release layer containing 5-HTP and carbidopa. In some embodiments hereof, the relationship between increasing the carbidopa dose and the increase in 5-HTP plasma exposure is non-linear. In some embodiments hereof, the relationship between increasing the carbidopa dose and the increase in 5-HTP plasma exposure is linear at lower carbidopa dose, and non-linear at higher carbidopa doses.

In some embodiments, a 1-fold increase in the carbidopa dose results in a <1-fold increase in 5-HTP exposure. In some embodiments, a 1-fold increase in the carbidopa dose results in a ~1-fold increase in 5-HTP exposure at lower carbidopa doses, and a <1-fold increase in 5-HTP exposure at higher carbidopa doses. In some embodiments, a fold increase in the carbidopa dose results in a lesser fold increase in 5-HTP exposure.

The 5-HTP plasma levels produced by the gastroretentive dosage form (e.g., when administered once or twice daily to a mammal, such as a human, optionally in a fed state) can at steady state be on average about 25 ng/ml to about 1000 ng/ml, depending on the combination of 5-HTP and carbidopa doses. In some embodiments, at twice daily dosing at steady state, the average 5-HTP plasma levels are above about 25 ng/ml. In some embodiments, at twice daily dosing at steady state, the average 5-HTP plasma levels are above about 50 ng/ml. In some embodiments, at steady state average 5-HTP plasma levels are above about 100 ng/ml. In some embodiments, the average 5-HTP plasma levels at steady state are above about 150 ng/ml. In some embodiments, the steady state average 5-HTP plasma levels are above about 200 ng/ml. In some embodiments, the steady state average 5-HTP plasma levels are above about 250 ng/ml. In some embodiments, the steady state average 5-HTP plasma levels are above about 300 ng/ml. In some embodiments, the steady state average 5-HTP plasma levels are above about 350 ng/ml. In some embodiments, the steady state average 5-HTP plasma levels are above about 400 ng/ml.

In some embodiments, the average 5-HTP plasma $T_{Max}$ produced by the gastroretentive dosage form (e.g., tablet) is delayed by about 1-fold to about 7-fold compared to 5-HTP administered in its native immediate release form (e.g., based on administration once or twice daily to a human, optionally in the fed state). In some embodiments, the average 5-HTP plasma $T_{Max}$ occurs at about 4 h, about 5 h, about 6 h, about 7 h, or about 8 h. In some embodiments, administration of the dosage form (e.g., tablet) once or twice daily to a mammalian subject, optionally a human, provides a time to achieve a maximum plasma concentration ($T_{Max}$) of 5-HTP that is delayed about 4 hours on average compared to an immediate release dosage form of 5-HTP.

The average carbidopa plasma levels produced by the gastroretentive dosage form (e.g., tablet) can at steady state be below about 25 ng/ml. In some embodiments, the average carbidopa plasma levels can be below about 20 ng/ml, about 15 ng/ml, about 10 ng/ml, about 5 ng/ml, about 2.5 ng/ml, or about 1 ng/ml. The average carbidopa $C_{Max}$ plasma levels produced by gastroretentive dosage form can at steady state be below about 25 ng/ml. In some embodiments, the average $C_{Max}$ plasma levels produced by the presently disclosed subject matter can at steady state be below about 20 ng/ml, about 15 ng/ml, about 10 ng/ml, about 5 ng/ml, about 2.5 ng/ml, or about 1 ng/ml.

The gastroretentive dosage form (e.g., tablet) of the presently disclosed subject matter can, in some embodiments, increase the terminal half-life ($T_{1/2}$) as compared to when 5-HTP is administered in its native immediate release form for a given dose. In some embodiments, administration of the dosage form (e.g., tablet) once or twice daily to a mammalian subject, optionally a human, provides an increased 5-HTP half-life compared to a 5-HTP half-life when 5-HTP is administered in an immediate release form. In some embodiments, the 5-HTP half-life is increased by about 10% to about 200% compared to the 5-HTP half-life when the 5-HTP is administered in an immediate release form. In some embodiments, the $T_{1/2}$ is extended by about 10%, about 20%, about 30%, about 40%, about 50%, about 60%, about 70%, about 80%, about 90%, or about 100%. In some embodiments, the $T_{1/2}$ is extended by about 100% to about 200%. In some embodiments the $T_{1/2}$ is about 3.2 h, about 3.5 h, about 4 h, about 4.5 h, about 5 h, about 5.5 h, or about 6 h.

The presently disclosed gastroretentive dosage form can thus be administered orally and can act therapeutically by increasing plasma 5-HTP levels over baseline in a continuous manner, all or most of the time. In some embodiments, the 5-HTP plasma levels are increased continuously with the least possible variation in levels over time. Without being bound to any one theory, it is believed that, as 5-HTP crosses the blood brain barrier, the increased plasma 5-HTP can increase brain serotonin (i) synthesis, (ii) levels, and (iii) neurotransmission. More particularly, it is believed that an increase in the levels of extracellular serotonin can cause increased stimulation of serotonin receptors. The totality of this receptor stimulation can cause the increased serotonin neurotransmission. As described hereinabove, there is support for the therapeutic relevance of increased serotonin neurotransmission using 5-HTP dosage forms in a range of human disorders.

Accordingly, in some embodiments, the presently disclosed subject matter provides for the use of the disclosed gastroretentive dosage form for therapeutic use in a subject in need thereof. In some embodiments, the subject is a human. The gastroretentive sustained-release tablet formulation can be administered once or twice daily. The administration can occur at any time of the day. In some embodiments, administration is in the morning and evening, with or after (e.g., within about 15 minutes after) the morning and evening meal, respectively. In some embodiments, the interval between administrations at twice daily dosing is about 12 hours, but the interval can be longer or shorter. In some embodiments, the gastroretentive dosage form is administered to the subject in need during or after a meal. In some embodiments, the twice daily administration occurs during or after the morning and evening meals. In some embodiments, the twice daily administration occurs after the two highest caloric content or highest fat content meals of the day, e.g., breakfast and dinner, lunch and dinner, or breakfast and lunch.

In some embodiments, the gastroretentive dosage form (e.g., tablet) is administered once daily, e.g., during or after the meal with the highest caloric content of the day and/or during or after the meal with the highest fat content.

In some embodiments, the gastroretentive dosage form (e.g., tablet) is administered once, twice, or thrice daily. In some embodiments, the gastroretentive dosage form (e.g., tablet) is administered more than thrice daily.

In some embodiments, the presently disclosed gastroretentive dosage form (e.g., tablet) is used therapeutically with one or more other drugs.

In some embodiments, the gastroretentive dosage form is used as adjunctive therapy to a serotonin reuptake inhibitor when therapy with a serotonin reuptake inhibitor alone provides inadequate therapeutic relief. 5-HTP is known to synergize with serotonin reuptake inhibitors in elevating extracellular serotonin in the mammalian brain (Jacobsen et al, 2016a). I.e., under some circumstances the increase in brain extracellular serotonin consequent to combined 5-HTP and serotonin reuptake inhibitor administration is larger than the sum of the increases in brain extracellular serotonin consequent to 5-HTP and the serotonin reuptake inhibitor administered individually. Thereby, the presently disclosed gastroretentive dosage form can be used to significantly augment the pharmacological effect of serotonin reuptake inhibitor therapy.

In some embodiments, the effective therapeutic plasma 5-HTP levels consequent to administration of the presently disclosed gastroretentive dosage form is lower when used as adjunctive therapy to serotonin reuptake inhibitor therapy, as compared to when the gastroretentive dosage form is used as monotherapy. In further embodiments, therapeutic efficacy can be achieved using a lower dose of the serotonin reuptake inhibitor during co-therapy with the presently disclosed gastroretentive dosage form. In some embodiments, there is an interval between administration of the presently disclosed gastroretentive dosage form and administration of the serotonin reuptake inhibitor, to enhance tolerability of the combined therapy. A convenient mode is to administer the serotonin reuptake inhibitor before and the gastroretentive dosage form after a given meal. In different embodiments, said interval is 0.5 h, 1 h, 2 h, 3 h, 4 h, or longer.

Some disorders can require high continuous 5-HTP plasma exposure, in which case more than one unit per administration of the gastroretentive dosage form (e.g., tablet) can be necessary. In some embodiments, two, three, four, or more dosage form (e.g., tablets) can be administered over one, two, three, or more daily administrations.

In some embodiments, to optimize safety and/or tolerability of the presently disclosed gastroretentive dosage form in a subject in the need hereof, a dose up-titration scheme can be used to gradually elevate 5-HTP plasma level, over days, weeks, or months. In some embodiments, the dose up-titration is achieved by initiating treatment administering tablets with lower levels of carbidopa, e.g., 0.3125 mg, whereafter a first interval tablets with higher carbidopa levels, e.g., 0.625 mg, are administered for a second interval. This dose up-titration approach can be extended with a third, fourth, fifth, and so forth interval, using tablets with increasing levels of carbidopa. Interval length can be one to several days, or one to several weeks, as required. In some embodiments, the dose up-titration is individualized to the patient, e.g., to optimize the subject's safety, tolerability, and clinical response. In some instances, the dose up-titration involves administering only one tablet per day for a first interval, followed by two or more daily administrations for a second and subsequent intervals. Analogous, dose down-titration can be achieved, in a subject in need thereof, by administering tablets of descending carbidopa dose strength, over one, two, three, or several intervals, and/or by reducing the number of daily tablets administered. Down-titration can for many pharmaceuticals, including pro-serotonergic drugs, minimize discontinuation symptoms (Haddad, 1998).

In some embodiments, the gastroretentive dosage form is used to treat a specific disorder, non-limiting examples of which include social anxiety, panic disorder, generalized anxiety disorder, obsessive compulsive disorder (OCD), mood symptoms and agitation related to neurological disorders (e.g. Alzheimer's, Parkinson's), stroke recovery, premenstrual dysphoria, post-traumatic stress disorder, postpartum depression, depression after interferon treatment, eating disorders, obesity, irritable bowel syndrome-constipation, idiopathic constipation, and other constipation disorders. Moreover, in some embodiments the gastroretentive dosage form is used to treat indications where the pathogenesis is associated with low brain serotonin, non-limiting examples of which include impulse control disorders, aggression, suicidality, borderline personality disorder, autism, phenylketonuria, and tetrahydrobiopterin deficiency.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Manufacture of 5-HTP/Low-Dose Carbidopa Gastroretentive Tablets

Four compositions of the 5-HTP/low-dose carbidopa gastroretentive tablet technology were formulated and manufactured as bilayer tablets. See Table 1, below. The tablet weight was about 1000 mg total. The shape of the dry tablet was an oval, 18.9 mm long, 9.6 mm wide, 7 mm deep, with a beveled edge. Both the swelling layer and modified release layer weighed about 500 mg.

The tablets were manufactured from separate blends for the swelling and modified release layers, with each layer being filled and compressed in succession to the other in a tablet tooling die, to obtain a bilayer tablet. Each excipient was sieved and added to the appropriate blend (swelling or modified release).

In the modified-release layer blend the 5-HTP and carbidopa ingredients were added to the fillers and dry rinsing was performed. Prior, to obtain carbidopa content uniformity in the blend meeting the requirements of USP <905>, carbidopa was mixed with small amounts of microcrystalline cellulose (MCC) to create a first "pre-blend". If necessary, i.e., at low levels of carbidopa, the first pre-blend was mixed with an additional amount of MCC, creating a second pre-blend. This process was optionally repeated several times, creating several intermediate pre-blends, to achieve carbidopa content uniformity. The final MCC/carbidopa pre-blend was mixed with 5-HTP and the remaining modified release layer excipients, except sodium stearyl fumarate. This mixture was sieved through a 600 µm screen, whereafter sodium stearyl fumarate was mixed in. This was the final modified release layer blend.

In the swelling layer blend, all excipients were screened and mixed. This was the final swelling layer blend.

To produce the tablets, a manual tablet press (Natoli NP-RD10A (Natoli, Saint Charles, Mo., United States of America) was used. First, the modified release blend was filled and compressed into the die. Second, the swelling blend was filled into the die and compressed on top of the modified release layer, yielding the bilayer tablet. Tablet hardness was ~25 kp (22-28 kp)

While these tablets were prepared by a manual process, the same process can be fully automated on an automated bilayer press, e.g., a Manesty BB3B bilayer tablet press (Manesty, Knowsley, United Kingdom). A granulation process and addition of glidant can improve powder flow for use in an automated process and lubricated may be added to avoid sticking to machine components. Moreover, while these tablets were made by direct compression, the manufacturing of the tablets are easily adapted to high shear granulation, fluid bed granulation, or roller compaction, to potentially make more robust tablets and/or improve content uniformity, and to scale up manufacturing. The compositions of the swelling and modified release layers are shown in Table 1, below. 5-HTP levels were kept fixed at 250 mg per tablet. Carbidopa content was adjusted for the level of hydration of the carbidopa drug substance. The level of carbidopa per tablet (adjusted for hydration of the carbidopa drug substance) ranged from 0.3125 mg to 25 mg. Carbidopa content uniformity results are shown in Table 2, below.

TABLE 1

Composition of gastroretentive tablets of 5-HTP and low-dose carbidopa.

| | 0.3125 mg carbidopa Slow | | 25 mg carbidopa Slow | | 0.3125 mg carbidopa Fast | | 25 mg carbidopa Fast | |
|---|---|---|---|---|---|---|---|---|
| Material | % | g/batch | % | g/batch | % | g/batch | % | g/batch |
| Modified Release Layer Blend | | | | | | | | |
| 5-HTP | 50.00 | 50.0000 | 50.00 | 50.0000 | 50.00 | 50.0000 | 50.00 | 50.0000 |
| Carbidopa | 0.0676 | 0.0676[1] | 5.4054 | 5.4054[2] | 0.0676 | 0.0676[1] | 5.4054 | 5.4060[2] |
| Microcrystalline Cellulose PH102 | 11.1324 | 11.1324 | 5.7946 | 5.7946 | 25.1324 | 25.1324 | 19.7940 | 19.7940 |
| Polyox 301 | 5.00 | 5.0000 | 5.00 | 5.0000 | 5.00 | 5.0000 | 5.00 | 5.0000 |
| Release modifying polymers: Hypromellose K4M DC | 7.00 | 7.0000 | 7.00 | 7.0000 | 18.00 | 18.0000 | 18.00 | 18.0000 |
| Release modifying polymers: Hypromellose K100M CR | 25.00 | 25.0000 | 25.00 | 25.0000 | 0.00 | 0.00 | 0.00 | 0.00 |
| Butylated hydroxytoluene (BHT) | 0.20 | 0.2000 | 0.20 | 0.2000 | 0.20 | 0.2000 | 0.20 | 0.2000 |
| Silica Colloidal Anhydrous | 0.10 | 0.1000 | 0.10 | 0.1000 | 0.10 | 0.1000 | 0.10 | 0.1000 |
| Sodium Stearyl Fumarate | 1.50 | 1.5000 | 1.50 | 1.5000 | 1.50 | 1.5000 | 1.50 | 1.5000 |
| Total | 100.00 | 100.0000 | 100.00 | 100.0000 | 100.00 | 100.0000 | 100.00 | 100.0000 |
| Modified Release Layer Weight | | | | 500.00 mg | | | | |
| Swelling Layer Blend | | | | | | | | |
| Polyox Coagulant | 49.50 | 49.5000 | 49.50 | 49.5000 | 49.50 | 49.5000 | 49.50 | 49.5000 |
| Hypromellose K100M CR | 49.50 | 49.5000 | 49.50 | 49.5000 | 49.50 | 49.5000 | 49.50 | 49.5000 |
| Sodium Stearyl Fumarate | 1.00 | 1.0000 | 1.00 | 1.0000 | 1.00 | 1.0000 | 1.00 | 1.0000 |
| Total | 100.00 | 100.0000 | 100.00 | 100.0000 | 100.00 | 100.0000 | 100.00 | 100.0000 |
| Swelling Layer Weight | | | | 500.00 mg | | | | |
| Total Tablet Weight | | | | 1000.00 mg | | | | |

[1]Accounted for water content 0.3125 mg/0.925 = 0.338 mg
[2]Accounted for water content 25.0000 mg/0.925 = 27.0270 mg

TABLE 2

Carbidopa content uniformity test.

| | Results | | | |
|---|---|---|---|---|
| Test | Slow, 0.3125 mg carbidopa | Slow, 25.0 mg carbidopa | Fast, 0.3125 mg carbidopa | Slow, 25 mg carbidopa |
| Assay | 95.1% | 97.4% | 104.9% | 99.0% |
| | 1. 93.5% | 1. 99.3% | 1. 105.2% | 1. 99.8% |
| | 2. 97.2% | 2. 95.0% | 2. 103.5% | 2. 99.2% |
| | 3. 95.3% | 3. 99.9% | 3. 106.3% | 3. 97.9% |
| | 4. 95.8% | 4. 97.0% | 4. 108.6% | 4. 102.4% |
| Carbidopa | 5. 99.9% | 5. 96.6% | 5. 108.2% | 5. 99.9% |
| Uniformity | 6. 95.5% | 6. 95.8% | 6. 103.2% | 6. 97.9% |
| of Dosage | 7. 94.0% | 7. 98.7% | 7. 104.9% | 7. 97.2% |
| 10 Tablets | 8. 93.2% | 8. 96.3% | 8. 102.7% | 8. 100.1% |
| | 9. 92.5% | 9. 97.4% | 9. 101.5% | 9. 94.1% |
| | 10. 94.0% | 10. 98.0% | 10. 104.7% | 10. 101.5% |
| | AV = 8.7 | AV = 4.9 | AV = 8.9 | AV = 5.7 |
| | % RSD = 2.3% | % RSD = 1.6% | % RSD = 2.2% | % RSD = 2.4% |

Figure 1A:
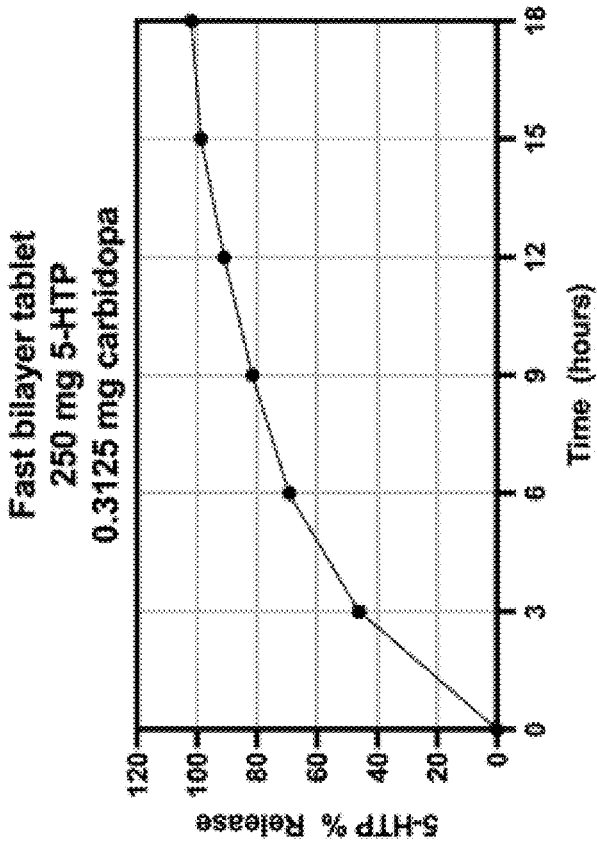
Figure 1D:
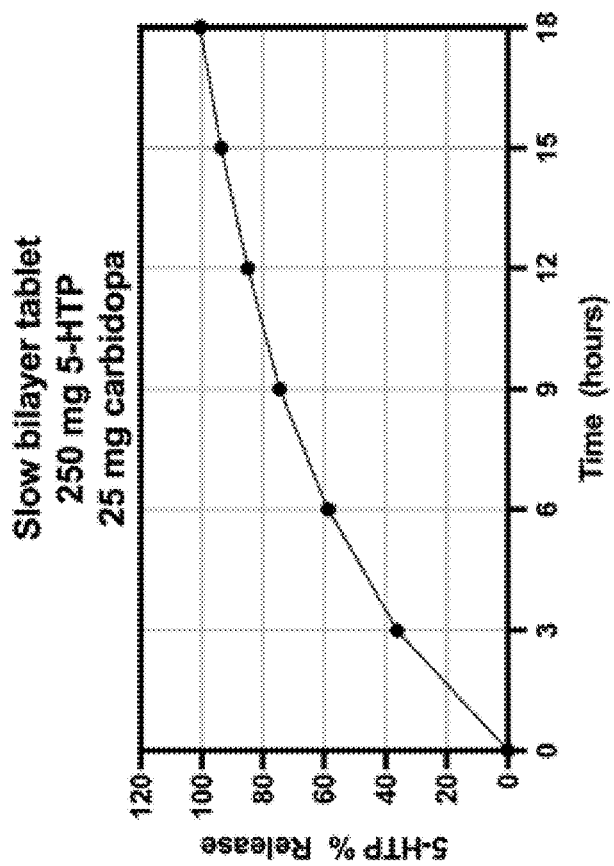
Figure 1C:
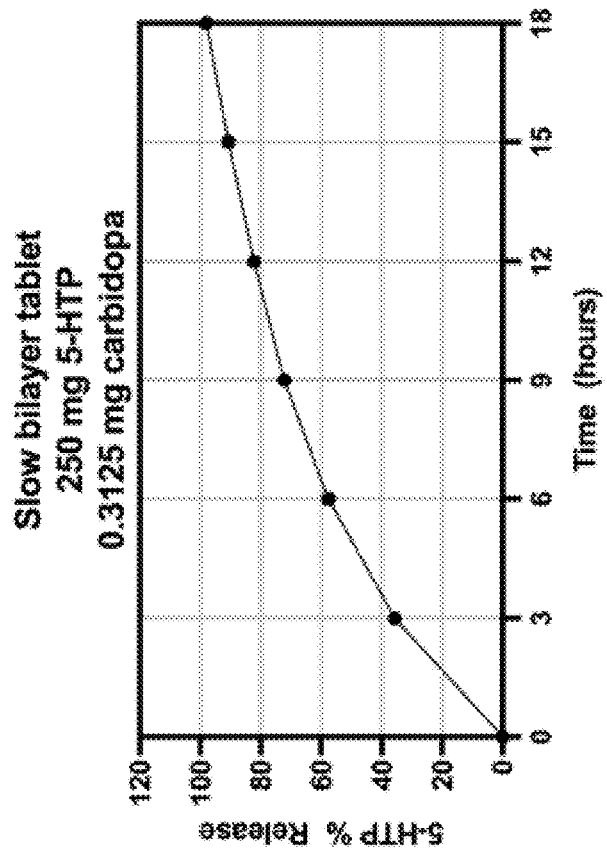
Figure 2:
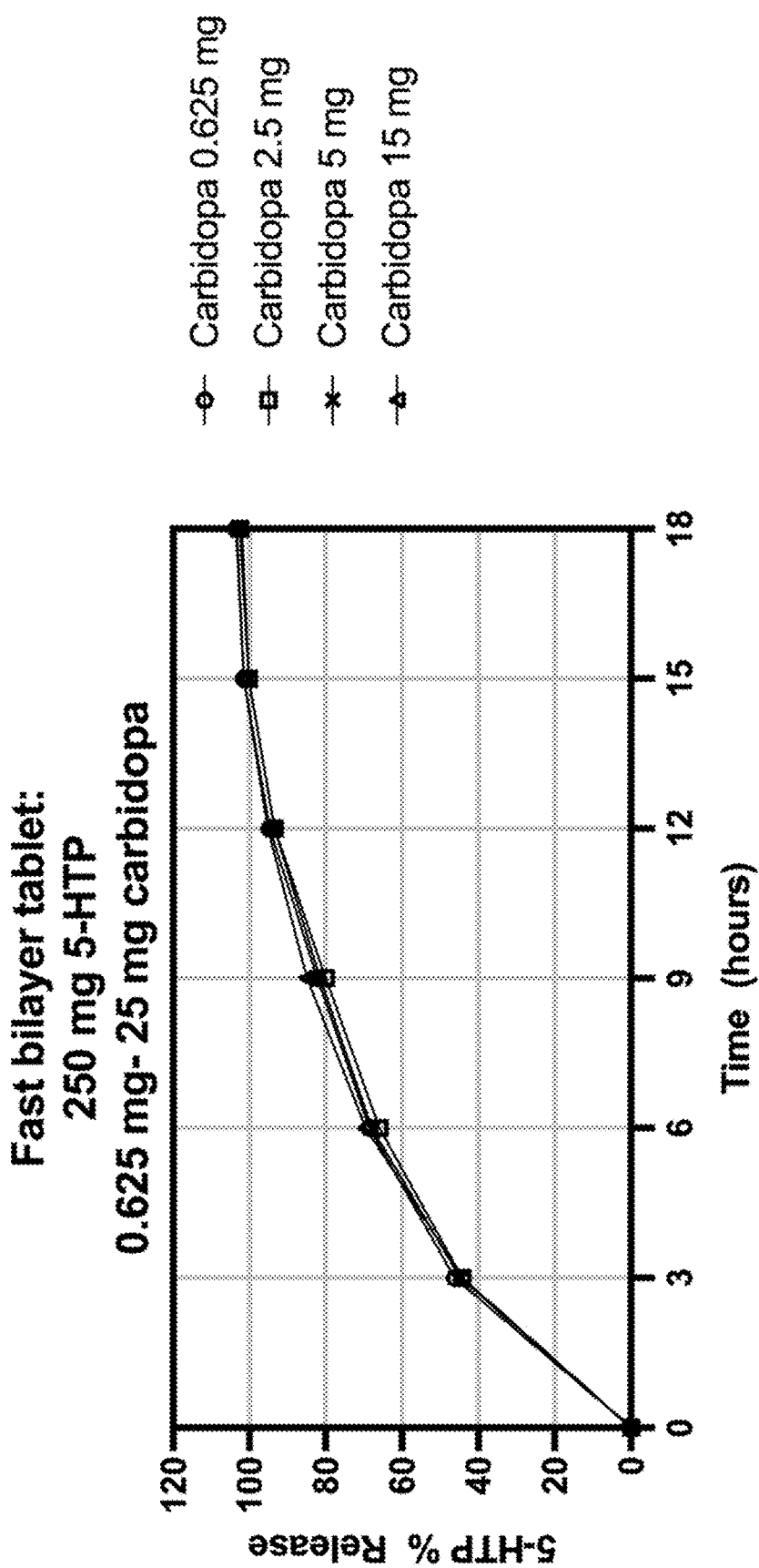
FIG. 2: Dissolution testing of "fast" 5-HTP/low-dose carbidopa gastroretentive tablets in vitro—Effect of carbidopa levels on 5-HTP release. Conditions: USP III (Reciprocating Cylinder) Dissolution Bath. 250 mL of 0.1 M HCl+0.02% disodium EDTA. 37° C.±0.5.
Figures 3A, 3B:
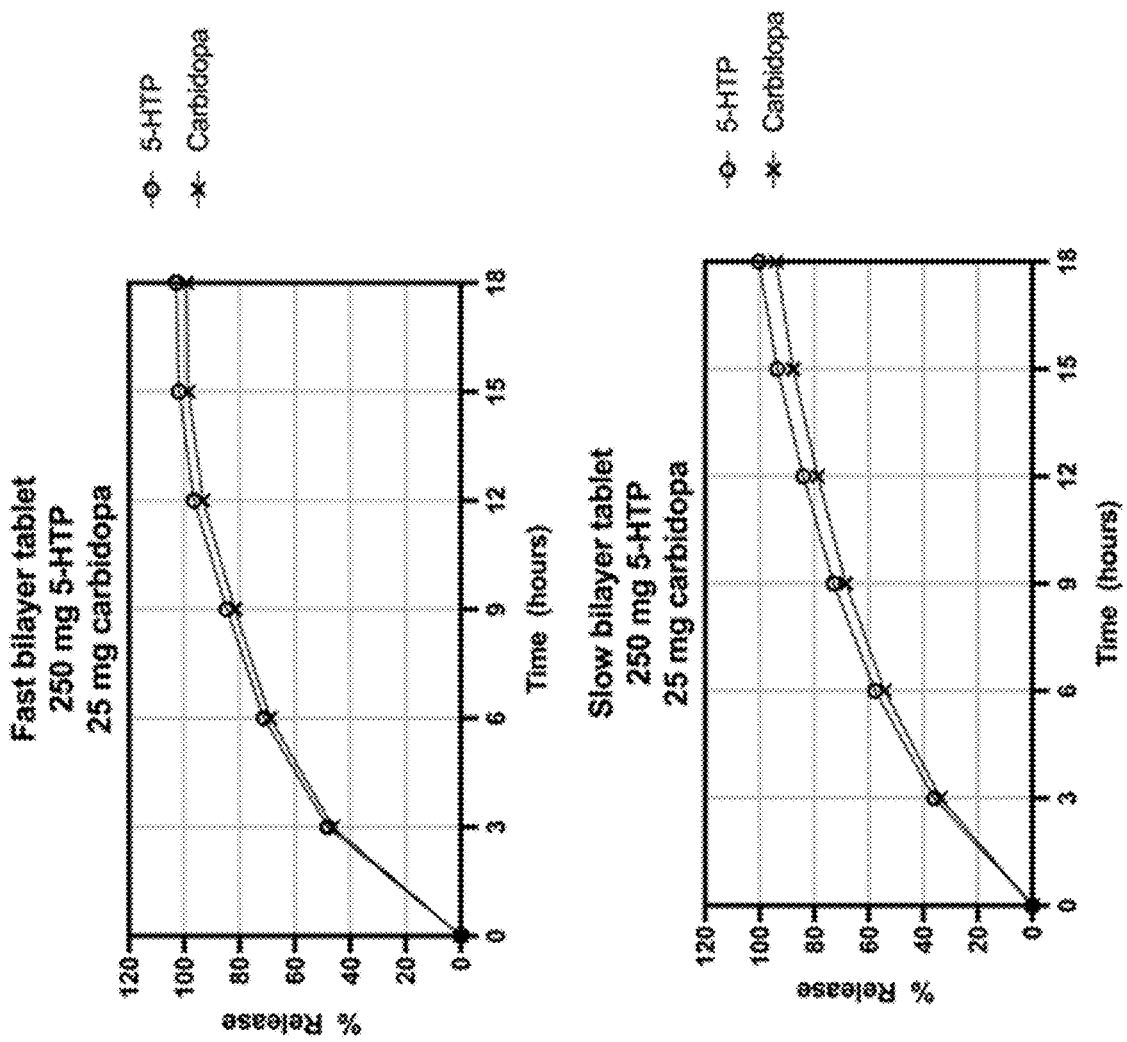
FIGS. 3A-3C: Dissolution testing of "fast" 5-HTP/low-dose carbidopa gastroretentive tablets in vitro—Parallel release of 5-HTP and carbidopa across formulations.
Figure 3C:
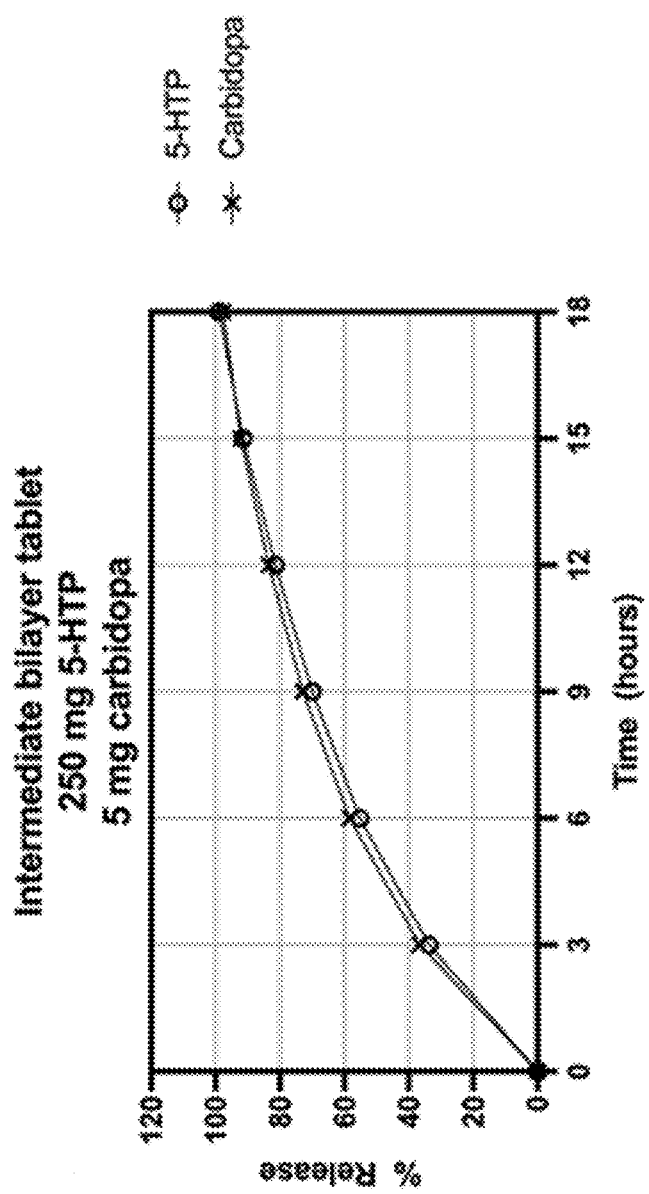

The release rate of 5-HTP from the modified release layer when combined with the swelling layer in a bilayer tablet varied from to T80%~8 hours (h) ("fast", see FIGS. 1A-1B) to T80%~11 h ("slow") (see FIGS. 1C-1D) under dissolution testing using a USP III apparatus (Agilent BIO-DIS reciprocating cylinder apparatus 3/7 system including 850-DS dissolution sampling station (auto sampler)). T80% is the time when 80% of the compound (5-HTP or carbidopa) has been released from the dosage form. The release rate was controlled by varying the levels of HPMC K100M CR and HPMC K4M DC in the modified release layer, and adjusting the MCC level to maintain the modified release layer weight of 500 mg. See Table 1. Increasing or decreasing the carbidopa level was compensated for by decreasing or increasing, respectively, MCC level to maintain the modified release layer weight of 500 mg. See Table 1. The level of carbidopa did not affect 5-HTP release rate. See FIG. 2. 5-HTP and carbidopa release rates were similar and in parallel, irrespective of overall release rates ("fast", "slow", or "intermediate") and carbidopa level. See FIGS. 3A-3C.

See also, Table 6, in Example 3, below. For all composition iterations of the bilayer tablet the 5-HTP and carbidopa T=80% differed <2 h hours.

During disintegration testing (Copley DTG 2000 Disintegration tester with disk which complies to USP <701> ("Disintegration" (2019)) the swelling layer stayed largely intact (i.e., in one piece, without significant erosion) and the modified release layer (although diminishing in size due to erosion) stayed attached the swelling layer for at least 8 hours. See FIG. 4.

Example 2

Short-Term Stability of 5-HTP/Low Dose Carbidopa Gastroretentive Tablets

Figure 5A:
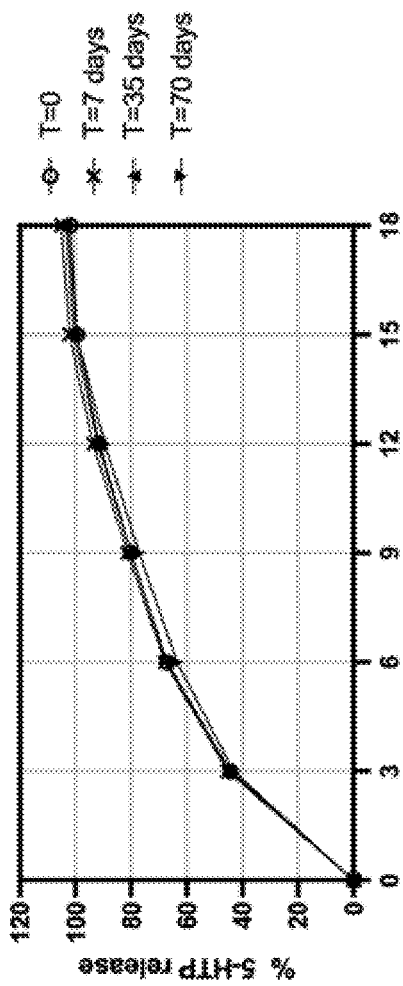
FIGS. 5A-5E: Dissolution testing of the "fast" 5-HTP/low-dose carbidopa gastroretentive tablets during a 70-day stability study.
Figure 5B:
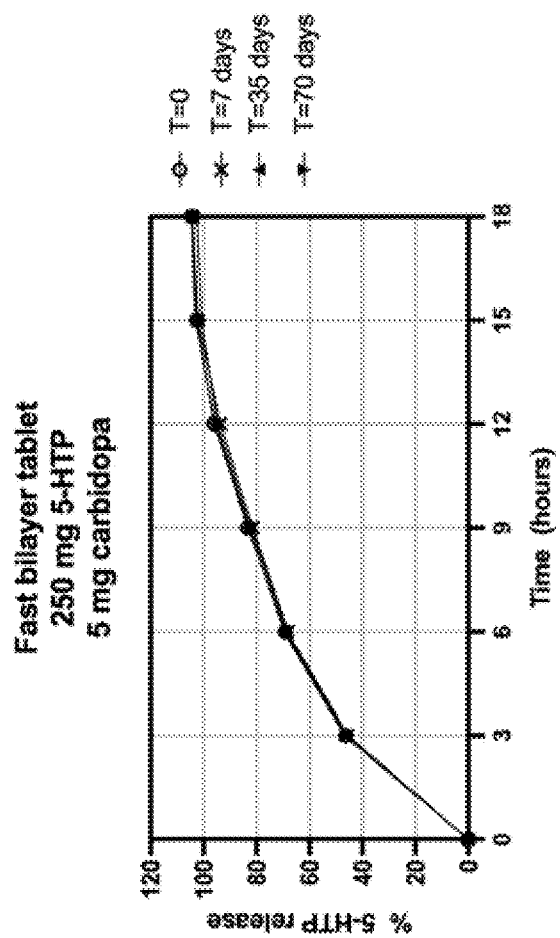
Figure 5C:
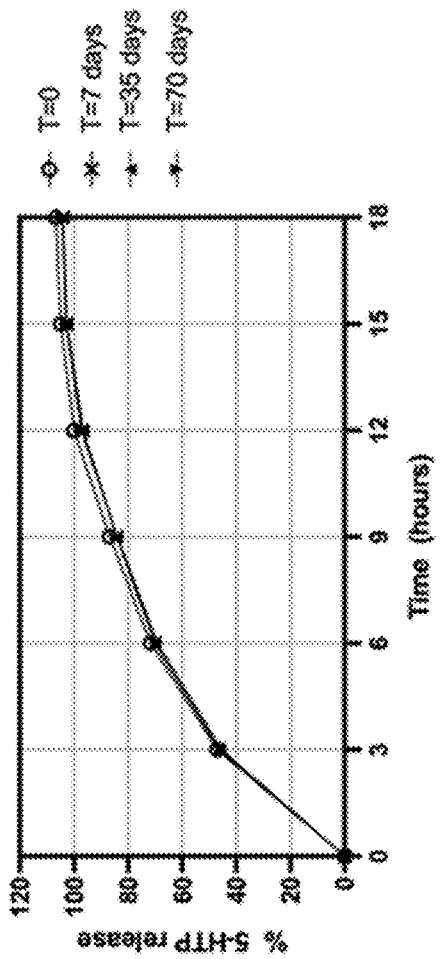
Figure 5D:
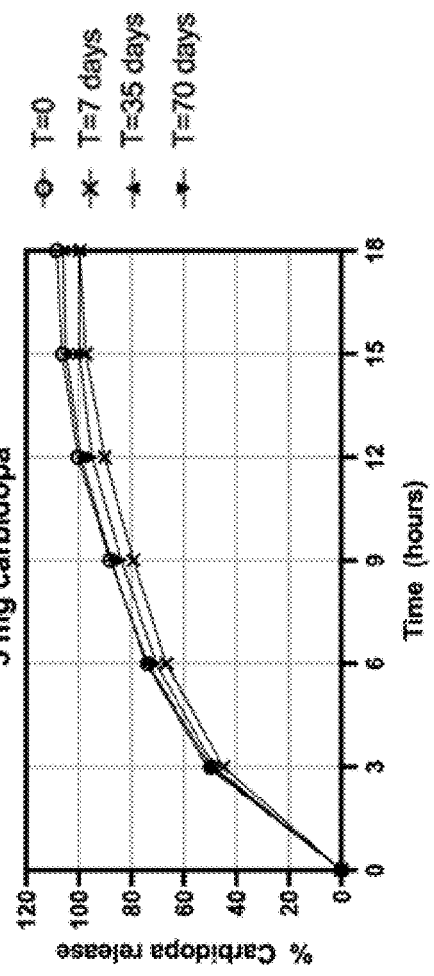
Figure 5E:
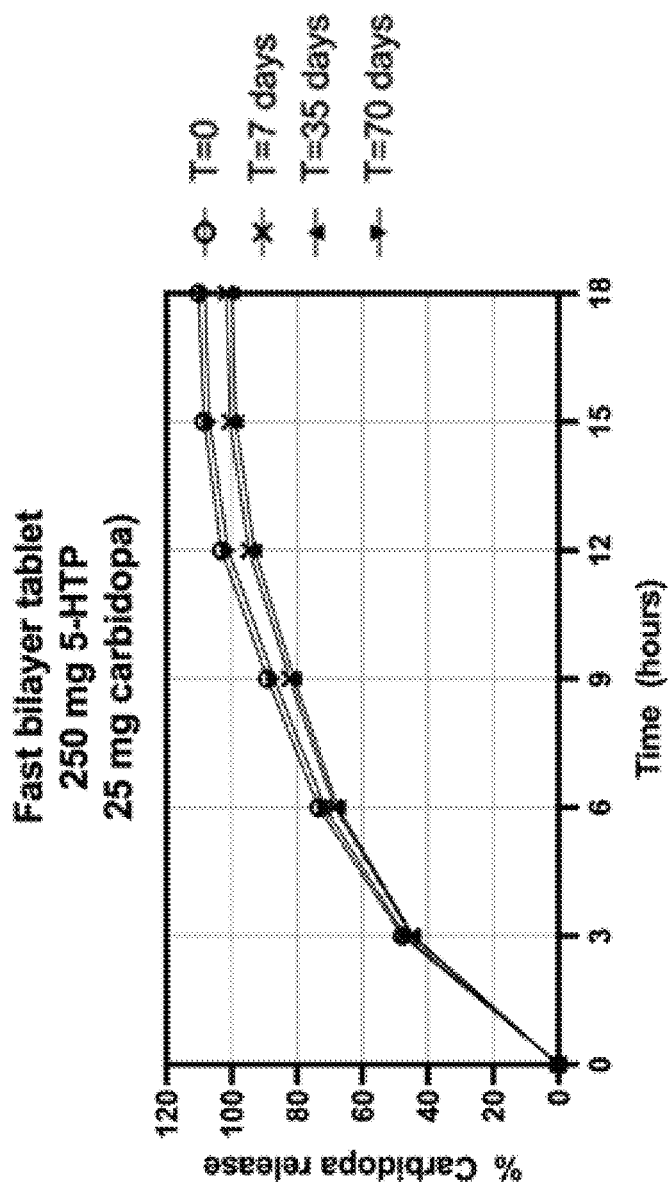

Three different carbidopa contents of bilayer tablets of the 5-HTP/low-dose carbidopa ("fast") gastroretentive composition were tested for short term stability (T=0, T=7 days, T=35 days, and T=70 days). For the modified release layer, "stable" was defined as meeting all acceptance criteria defined in Tables 3-5. The three bilayer tablets comprised 250 mg 5-HTP/0.625 mg carbidopa, 250 mg 5-HTP/5 mg carbidopa, and 250 mg 5-HTP/25 mg carbidopa. Assay and related substances were determined on single modified release monolayers, as swelling layer excipients interfered with assay and related substances for 5-HTP and carbidopa. Assay for 5-HTP and carbidopa were within 90.0-110.0% nominal at all stability time points for all three tablets. Related substances for 5-HTP and carbidopa remained within acceptance criteria at all stability time points for all three tablets. Appearance remained unchanged as a white to off-white bilayer tablet for all bilayer tablets. See Tables 3-5, below. Dissolution profiles of 5-HTP and carbidopa from the three bilayer tablets were tested using a USP III apparatus. See FIGS. 5A-5E. The dissolution profiles of 5-HTP for all three bilayer tablets at 70 days were indistinguishable from the profiles at T=0. See FIGS. 5A-5C and Tables 3-5. The dissolution profiles of carbidopa for the 250 mg 5-HTP/5 mg carbidopa and 250 mg 5-HTP/25 mg bilayer tablets were indistinguishable from the profiles at T=0 (the carbidopa levels from the 250 mg 5-HTP/0.625 mg carbidopa bilayers were too low to be reliably quantified). See FIGS. 5D and 5E.

TABLE 3

Short-term stability of "fast" 250 mg 5-HTP/0.625 mg carbidopa gastroretentive tablet.

| Test | Method | Acceptance Criteria | | Results | |
|---|---|---|---|---|---|
| | | | | T = 0 | 7 days |
| Identity | HPLC/UV | Retention time comparable to reference standard | | Complies | Complies |
| Assay | HPLC/UV | 90.0-110.0% nominal | | 5-HTP: 97.2% Carbidopa: 95.3% | 5-HTP: 99.4% Carbidopa: 99.4% |
| Related Substances[1] | HPLC/UV | 5-HTP Report ≥ 0.05% Unspecified Impurities NMT 0.5% Total Impurities NMT 3.0% | Carbidopa Report ≥ 0.10% Unspecified Impurities NMT 0.5% Total Impurities NMT 3.0% | 5-HTP Tryptophan: 0.13% Total: 0.13% | Carbidopa Not reported | 5-HTP Tryptophan: 0.11% Total: 0.11% | Carbidopa Not reported |
| Uniformity of Dosage Units | HPLC/UV | AV ≤ 15.0 | | 5-HTP: 3.8 Carbidopa: 8.0 | Not tested |

Test on Bilayer tablets

| Appearance | Visual | White to off white bilayer tablet (one layer maybe slightly speckled) | White to off white bilayer tablet (one layer maybe slightly speckled) | White to off white bilayer tablet (one layer maybe slightly speckled) |
|---|---|---|---|---|
| Dissolution (5-HTP) | HPLC/UV | Report results | 3 hours = 44.4% 6 hours = 67.3% 9 hours = 80.1% 12 hours = 91.5% 15 hours = 99.5% 18 hours = 101.9% | 3 hours = 45.4% 6 hours = 68.0% 9 hours = 81.4% 12 hours = 93.8% 15 hours = 102.3% 18 hours = 105.1% |

| Test | Method | Acceptance Criteria | | Results | |
|---|---|---|---|---|---|
| | | | | 35 days | 70 days |

Test on Single modified release layers

| Identity | HPLC/UV | Retention time comparable to reference standard | | Complies | Complies |
|---|---|---|---|---|---|
| Assay | HPLC/UV | 90.0-110.0% nominal | | 5-HTP: 98.9% Carbidopa: 97.7% | 5-HTP: 99.4% Carbidopa: 92.7% |
| Related Substances[1] | HPLC/UV | 5-HTP Report ≥ 0.05% Unspecified Impurities NMT | Carbidopa Report ≥ 0.10% Unspecified Impurities | 5-HTP Tryptophan: 0.11% Total: 0.11% | Carbidopa Not reported | 5-HTP Tryptophan: 0.11% Total: 0.11% | Carbidopa Not reported |

TABLE 3-continued

Short-term stability of "fast" 250 mg 5-HTP/0.625 mg carbidopa gastroretentive tablet.

|  |  |  |  |  |
|---|---|---|---|---|
|  |  | 0.5% Total Impurities NMT 3.0% | NMT 0.5% Total Impurities NMT 3.0% |  |  |
| Uniformity of Dosage Units | HPLC/UV | AV ≤ 15.0 | Not tested | Not tested |
|  |  | Test on Bilayer tablets |  |  |
| Appearance | Visual | White to off white bilayer tablet (one layer maybe slightly speckled) | White to off white bilayer tablet (one layer maybe slightly speckled) | White to off white bilayer tablet (one layer maybe slightly speckled) |
| Dissolution (5-HTP) | HPLC/UV | Report results | 3 hours = 44.6%<br>6 hours = 67.1 %<br>9 hours = 80.3%<br>12 hours = 92.0%<br>15 hours = 100.7%<br>18 hours = 103.6% | 3 hours = 43.2%<br>6 hours = 63.6%<br>9 hours = 77.2%<br>12 hours = 89.6%<br>15 hours = 99.7%<br>18 hours = 102.8% |

NMT = Not More Than;
[1]Related substance for carbidopa to be tested on tablets containing ≥ 5 mg carbidopa

TABLE 4

Short-term stability of "Fast" 250 mg 5-HTP/5 mg carbidopa gastroretentive tablet.

| | | | Results | |
|---|---|---|---|---|
| Test | Method | Acceptance Criteria | T = 0 | 7 days |
| | | Test on Single modified release layers | | |
| Identity | HPLC/UV | Retention time comparable to reference standard | Complies | Complies |
| Assay | HPLC/UV | 90.0-110.0% nominal | 5-HTP: 99.1%<br>Carbidopa: 97.7% | 5-HTP: 99.0%<br>Carbidopa: 95.0% |
| Related Substances | HPLC/UV | 5-HTP: Report ≥ 0.05% Unspecified Impurities NMT 0.5% Total Impurities NMT 3.0% / Carbidopa: Report ≥ 0.10% Unspecified Impurities NMT 0.5% Total Impurities NMT 3.0% | 5-HTP: Tryptophan: 0.10% Serotonin: 0.17% Total: 0.27% / Carbidopa: Impurity A: 0.31% Impurity D + E: 0.22% Impurity H: 0.30% Total: 0.83% | 5-HTP: Tryptophan: 0.12% Total: 0.12% / Carbidopa: Impurity A: 0.30% Impurity D + E: 0.37% Impurity H: 0.23% Total: 0.90% |
| Uniformity of Dosage Units | HPLC/UV | AV ≤ 15.0 | 5-HTP: 1.2<br>Carbidopa: 6.1 | Not tested |
| | | Test on Bilayer tablets | | |
| Appearance | Visual | White to off white bilayer tablet (one layer maybe slightly speckled) | White to off white bilayer tablet (one layer maybe slightly speckled) | White to off white bilayer tablet (one layer maybe slightly speckled) |
| Dissolution (5-HTP) | HPLC/UV | Report results | 3 hours = 46.3%<br>6 hours = 69.3%<br>9 hours = 83.3%<br>12 hours = 96.2%<br>15 hours = 102.7%<br>18 hours = 104.3% | 3 hours = 45.6%<br>6 hours = 68.2%<br>9 hours = 81.6%<br>12 hours = 93.8%<br>15 hours = 102.2%<br>18 hours = 104.3% |

| | | | Results | |
|---|---|---|---|---|
| Test | Method | Acceptance Criteria | 35 days | 70 days |
| | | Test on Single modified release layers | | |
| Identity | HPLC/UV | Retention time comparable to reference standard | Complies | Complies |
| Assay | HPLC/UV | 90.0-110.0% nominal | 5-HTP: 99.2%<br>Carbidopa: 92.2 % | 5-HTP: 99.6%<br>Carbidopa: 91.4% |
| Related Substances | HPLC/UV | 5-HTP: Report ≥ 0.05% Unspecified / Carbidopa: Report ≥ 0.10% | 5-HTP: Tryptophan: 0.10% / Carbidopa: Impurity A: 0.22% | 5-HTP: Tryptophan: 0.07% / Carbidopa: RRT 0.62: 0.24% |

TABLE 4-continued

Short-term stability of "Fast" 250 mg 5-HTP/5 mg carbidopa gastroretentive tablet.

|  |  |  |  |  |  |  |
|---|---|---|---|---|---|---|
|  |  | Impurities NMT 0.5% Total Impurities NMT 3.0% | Unspecified Impurities NMT 0.5% Total Impurities NMT 3.0% | Total: 0.10% | Impurity D + E: 0.27% Impurity H: 0.27% Total: 0.90% | Serotonin: 0.11% Total: 0.18% | Impurity A: 0.24% Impurity H: 0.29% Total: 0.77% |
| Uniformity of Dosage Units | HPLC/UV | AV ≤ 15.0 | Not tested | Not tested |

Test on Bilayer tablets

| Appearance | Visual | White to off white bilayer tablet (one layer maybe slightly speckled) | White to off white bilayer tablet (one layer maybe slightly speckled) | White to off white bilayer tablet (one layer maybe slightly speckled) |
|---|---|---|---|---|
| Dissolution (5-HTP) | HPLC/UV | Report results | 3 hours = 46.9%<br>6 hours = 69.7%<br>9 hours = 83.1%<br>12 hours = 95.7%<br>15 hours = 103.1%<br>18 hours = 104.7% | 3 hours = 46.1%<br>6 hours = 68.5%<br>9 hours = 82.4%<br>12 hours = 95.0%<br>15 hours = 101.0%<br>18 hours = 102.6% |

NMT = Not More Than

TABLE 5

Short-term stability of 250 mg 5-HTP/25 mg carbidopa gastroretentive tablet.

|  |  |  | Results | |
|---|---|---|---|---|
| Test | Method | Acceptance Criteria | T = 0 | 7 days |

Test on Single modified release layers

| Identity | HPLC/UV | Retention time comparable to reference standard | Complies | Complies |
|---|---|---|---|---|
| Assay | HPLC/UV | 90.0-110.0% nominal | 5-HTP: 98.7%<br>Carbidopa: 94.7% | 5-HTP: 99.9%<br>Carbidopa: 96.5% |
| Related Substances | HPLC/UV | 5-HTP: Report ≥ 0.05% Unspecified Impurities NMT 0.5% Total Impurities NMT 3.0% / Carbidopa: Report ≥ 0.10% Unspecified Impurities NMT 0.5% Total Impurities NMT 3.0% | 5-HTP: Serotonin: 0.25%, L-Tryptophan: 0.12%, Total: 0.38% / Carbidopa: Impurity A: 0.27%, Total: 0.23% | 5-HTP: Serotonin: 0.18%, L-Tryptophan: 0.11%, Total: 0.29% / Carbidopa: Impurity A: 0.29%, Total: 0.29% |
| Uniformity of Dosage Units | HPLC/UV | AV ≤ 15.0 | 5-HTP: 2.2<br>Carbidopa: 6.5 | Not tested |

Test on Bilayer tablets

| Appearance | Visual | White to off white bilayer tablet (one layer maybe slightly speckled) | White to off white bilayer tablet (one layer maybe slightly speckled) | White to off white bilayer tablet (one layer maybe slightly speckled) |
|---|---|---|---|---|
| Dissolution (5-HTP) | HPLC/UV | Report results | 3 hours = 47.2%<br>6 hours = 71.8%<br>9 hours = 86.9%<br>12 hours = 100.1%<br>15 hours = 105.0%<br>18 hours = 106.7% | 3 hours = 45.0%<br>6 hours = 68.6%<br>9 hours = 82.4%<br>12 hours = 94.8%<br>15 hours = 100.7%<br>18 hours = 101.8% |

|  |  |  | Results | |
|---|---|---|---|---|
| Test | Method | Acceptance Criteria | 35 days | 70 days |

Test on Single modified release layers

| Identity | HPLC/UV | Retention time comparable to reference standard | Complies | Complies |
|---|---|---|---|---|
| Assay | HPLC/UV | 90.0-110.0% nominal | 5-HTP: 99.6%<br>Carbidopa: 92.2% | 5-HTP: 98.7%<br>Carbidopa: 95.8% |
| Related Substances | HPLC/UV | 5-HTP: Report ≥ 0.05% Unspecified / Carbidopa: Report ≥ 0.10% Unspecified | 5-HTP: Tryptophan: 0.10% / Carbidopa: Impurity A: 0.29% | 5-HTP: Serotonin: 0.28% / Carbidopa: Impurity A: 0.33% |

TABLE 5-continued

Short-term stability of 250 mg 5-HTP/25 mg carbidopa gastroretentive tablet.

|  |  | Impurities NMT 0.5% Total Impurities NMT 3.0% | Impurities NMT 0.5% Total Impurities NMT 3.0% | Total: 0.10% | Total: 0.29% | L-Tryptophan: 0.11% Total: 0.40% | Total: 0.33% |
|---|---|---|---|---|---|---|---|
| Uniformity of Dosage Units | HPLC/UV | AV ≤ 15.0 | | Not tested | | Not tested | |
|  |  | Test on Bilayer tablets | | | | | |
| Appearance | Visual | White to off white bilayer tablet (one layer maybe slightly speckled) | | White to off white bilayer tablet (one layer maybe slightly speckled) | | White to off white bilayer tablet (one layer maybe slightly speckled) | |
| Dissolution (5-HTP) | HPLC/UV | Report results | | 3 hours = 46.4% 6 hours = 70.2% 9 hours = 84.1% 12 hours = 96.7% 15 hours = 102.6% 18 hours = 104.0% | | 3 hours = 45.6% 6 hours = 69.2% 9 hours = 84.1% 12 hours = 97.3% 15 hours = 103.0% 18 hours = 104.4% | |

NMT = Not More Than

Example 3

Manufacture of Other 5-HTP/Low-Dose Carbidopa Gastroretentive Tablets

To further broaden the scope of the 5-HTP/low-dose carbidopa gastroretentive tablet technology presented in Example 1, a series of 33 compositions of bilayer tablets of differing swelling and modified release layers were prepared and characterized by dissolution testing as described under Example 1. See Table 6, below. Excipients not listed are identical to listed in Table 1. In the 29 of 33 compositions where the T=80% release was tested, the T=80% of 5-HTP and the T=80% of carbidopa differed by less than 2 hours, demonstrating essentially parallel release of 5-HTP and carbidopa.

TABLE 6

Summary of T80% for various 5-HTP/low-dose carbidopa gastroretentive tablets iterations.

| Formulation[1] | Swelling layer | | MR layer | | T = 80% | |
|---|---|---|---|---|---|---|
|  | HPMC | Polyox | HPMC | Polyox | Carbidopa | 5-HTP |
| 201140-052-01 | Not used | 100% Coagulant | 32% K100LVCR | 5% 301 | 8.8 h | 8.0 h |
| 201140-052-02 | Not used | 100% Coagulant | 18% K100LVCR | 5% 301 | 8.0 h | 7.0 h |
| 201140-052-03 | Not used | 100% Coagulant | 32% K4MCR | 5% 301 | Not achieved | Not achieved |
| 201140-052-04 | Not used | 100% Coagulant | 18% K4MCR | 5% 301 | 10.5 h | 8.8 h |
| 201140-056-05 | 49.5% K100M | 49.5% Coagulant | 18% K100LVCR | 5% 301 | 6.1 h | 5.5 h |
| 201140-056-06 | 49.5% K15M | 49.5% Coagulant | 18% K100LVCR | 5% 301 | 5.6 h | 5.4 h |
| 201140-056-01 | 19.8% K100M | 79.2% Coagulant | 18% K100LVCR | 5% 301 | Not tested | Not tested |
| 201140-056-03 | 49.5% K4M | 49.5% Coagulant | 18% K100LVCR | 5% 301 | Not tested | Not tested |
| 201140-057-01 | 49.5% K100M | 49.5% Coagulant | 18% K100LVCR | 5% 1105 | 4.7 h | 4.2 h |
| 201140-057-02 | 49.5% K100M | 49.5% Coagulant | 9% K100LVCR | 5% 301 | 4.6 h | 4.2 h |
| 201140-057-03 (with SLS) | 49.5% K100M | 49.5% Coagulant | 18% K100LVCR | 5% 301 | Not tested | Not tested |
| 201140-061-01 | 49.5% K100M | 49.5% Coagulant | 18% K4M | 5% 301 | 9.6 h | 8.7 h |
| 201140-061-02 | 49.5% K100M | 49.5% Coagulant | 25% K4M | 5% 301 | 10.2 h | 8.9 h |
| 201140-061-03 | 49.5% K100M | 49.5% Coagulant | 32% K100LV | 5% 301 | 5.8 h | 5.5 h |
| 201140-061-04 | 49.5% K100M | 49.5% Coagulant | 25% K100LV | 5% 301 | 5.8 h | 5.4 h |
| 201140-066-01 | 49.5% K100M | 49.5% Coagulant | 32% K4M | 5% 301 | 12.1 h | 11.5 h |
| 201140-066-02 | 49.5% K100M | 49.5% Coagulant | 25% K4M 7% K100M | 5% 301 | 13.3 h | 12 h |

TABLE 6-continued

Summary of T80% for various 5-HTP/low-dose carbidopa gastroretentive tablets iterations.

| | Swelling layer | | MR layer | | T = 80% | |
|---|---|---|---|---|---|---|
| Formulation[1] | HPMC | Polyox | HPMC | Polyox | Carbidopa | 5-HTP |
| 201140-066-03 | 49.5% K100M | 49.5% Coagulant | 15% K4M | 22% 301 | 12 h | 11 h |
| 201140-066-04 (Weight of Swelling layer is 400 mg) | 49.5% K100M | 49.5% Coagulant | 15% K4M 17% K100M | 5% 301 | 12.2 h | 11 h |
| 201140-072-01 | 49.5% K100M | 49.5% Coagulant | 15% K4M 17% K100M | 5% 301 | 13.6 h | 12 h |
| 201140-072-02 | 49.5% K100M | 49.5% Coagulant | 7% K4M 25% K100M | 5% 301 | 14.6 h | 13 h |
| 201140-072-03 | 49.5% K100M | 49.5% Polyox 303 | 7% K4M 25% K100M | 5% 301 | 15 h | 13.6 h |
| 201140-072-04 | 49.5% K100M | 49.5% Polyox 303 | 25% K4M 7% K100M | 5% 301 | 13.1 h | 12 h |
| 201140-076-01 | 49.5% K100M | 49.5% Coagulant | 25% K4M | 5% 301 | 11.2 h | 10.7 h |
| 201140-076-02 | 49.5% K100M | 49.5% Coagulant | 7% K4M 25% K100M | 5% 301 | 13.8 h | 13.3 h |
| 201140-076-03 | 49.5% K100M | 49.5% Coagulant | 25% K4M 3.5% K100M | 5% 301 | 12.3 h | 11.8 h |
| 201140-076-04 | 49.5% K100M | 49.5% Coagulant | 28.5% K4M | 5% 301 | 12.0 h | 11.5 h |
| 201140-080-01 | 49.5% K100M | 49.5% Coagulant | 18% K4M | 5% 301 | 8.7 h | 8.0 h |
| 201140-080-02 | 49.5% K100M | 49.5% Coagulant | 13% K4M | 5% 301 | 8.6 h | 8.1 h |
| 201140-082-01 | 49.5% K100M | 49.5% Coagulant | 7% K4M 25% K100M | 5% 301 | 14 h | 13 h |
| 201140-082-02 | 49.5% K100M | 49.5% Coagulant | 18% K4M | 5% 301 | 10.3 h | 10 h |
| 201140-091-01 (250 mg 5-HTP, 2.5 mg carbidopa, 1000 mg tablet) | 49.5% K100M | 49.5% Coagulant | 7% K4M 25% K100M | 5% 301 | 13.1 h | 12.4 h |
| 201140-091-02 (250 mg 5-HTP, 2.5 mg carbidopa, 1000 mg tablet weight) | 49.5% K100M | 49.5% Coagulant | 18% K4M | 5% 301 | 9 h | 8.9 h |

SLS = Sodium lauryl sulfate

Formulations had been prepared at 300 mg 5-HTP, 25 mg carbidopa with a total 1200 mg tablet weight (swelling layer 600 mg, modified release layer 600 mg) up until formulation 201140-082 series. After that tablet weight was reduced from 1200 mg to 1000 mg (swelling layer 500 mg, modified release layer 500 mg), with 250 mg 5-HTP and 2.5 mg carbidopa.

Example 4

Excipient Compatibility

Excipient compatibility studies were performed to examine the stability of 5-HTP and carbidopa mixed together, either the two APIs alone or in the presence of one or two excipients. The stability (assay and level of impurities) was tested using small aliquots of 5-HTP (300 mg) and carbidopa (25 mg) blended together, with or without together excipients. See Table 7, below. The API/excipient ratios were based on the approximate composition of gastroretentive tablets of 5-HTP and carbidopa in Table 1. There were no significant increases in the levels of impurities for any of the API/excipient(s) combinations at T=0, 7 days and 1 month of storage at 40° C. See Table 8, below. The maximum percentage increase (largest single impurity) for carbidopa was 0.44%, 0.55%, and 0.86% at T=0, 7 days and 1 month, respectively. The maximum percentage increase for 5-HTP was 0.27%, 0.48%, and 0.49% at T=0, 7 days and 1 month, respectively.

TABLE 7

Excipient compatibility of 5-HTP and carbidopa in a range of excipients.

| Sample | Components | Weight (mg) |
|---|---|---|
| 1 | 5-HTP | 300.00 |
| | Carbidopa | 25.00 |
| | Butylated hydroxytoluene (BHT) | 0.65 |
| 2 | 5-HTP | 300.00 |
| | Carbidopa | 25.00 |
| | Ascorbic Acid | 0.65 |

TABLE 7-continued

Excipient compatibility of 5-HTP and carbidopa in a range of excipients.

| Sample | Components | Weight (mg) |
|---|---|---|
| 3 | 5-HTP | 300.00 |
|  | Carbidopa | 25.00 |
|  | Butylated hydroxytoluene (BHT) | 3.25 |
| 4 | 5-HTP | 300.00 |
|  | Carbidopa | 25.00 |
|  | Ascorbic Acid | 3.25 |
| 5 | 5-HTP | 300.00 |
|  | Carbidopa | 25.00 |
| 6 | 5-HTP | 300.00 |
|  | Carbidopa | 25.00 |
|  | PVP K30 | 16.25 |
| 7 | 5-HTP | 300.00 |
|  | Carbidopa | 25.00 |
|  | Polyox WSR 301 | 16.25 |
| 8 | 5-HTP | 300.00 |
|  | Carbidopa | 25.00 |
|  | Polyox WSR 301 | 16.25 |
|  | BHT | 0.65 |
| 9 | 5-HTP | 300.00 |
|  | Carbidopa | 25.00 |
|  | Polyox WSR 301 | 16.25 |
|  | Ascorbic Acid | 0.65 |
| 10 | 5-HTP | 300.00 |
|  | Carbidopa | 25.00 |
|  | Polyox WSR 301 | 16.25 |
|  | BHT | 3.25 |
| 11 | 5-HTP | 300.00 |
|  | Carbidopa | 25.00 |
|  | Polyox WSR 301 | 16.25 |
|  | Ascorbic Acid | 3.25 |
| 12 | 5-HTP | 300.00 |
|  | Carbidopa | 25.00 |
|  | Magnesium Stearate | 6.5 |
|  | BHT | 0.65 |
| 13 | 5-HTP | 300.00 |
|  | Carbidopa | 25.00 |
|  | Sodium stearyl fumarate | 6.5 |
| 14 | 5-HTP | 300.00 |
|  | Carbidopa | 25.00 |
|  | Silica Colloidal Anhydrous (Aerosil 200) | 6.5 |
| 15 | 5-HTP | 300.00 |
|  | Carbidopa | 25.00 |
|  | Amberlite IRP 69 resin | 6.5 |
|  | BHT | 0.65 |
| 16 | 5-HTP | 300.00 |
|  | Carbidopa | 25.00 |
|  | Amberlite IRP 69 resin | 6.5 |
| 17 | 5-HTP (control) | 300.00 |
| 18 | Carbidopa (control) | 25.00 |
| 19 | 5-HTP | 300.00 |
|  | Carbidopa | 25.00 |
|  | Magnesium Stearate | 6.5 |
| 20 | 5-HTP | 300.00 |
|  | Carbidopa | 25.00 |
|  | Sodium stearyl fumarate | 6.5 |
|  | BHT | 0.65 |

TABLE 8

Summary of API and Excipient Compatibility Results.

| | Carbidopa | | | | | | 5-HTP | | | | | |
|---|---|---|---|---|---|---|---|---|---|---|---|---|
| | Impurities at T = 0 (%) | | Impurities at T = 7 (%) | | Impurities at T = 1 month (%) | | Impurities at T = 0 (%) | | Impurities at T = 7 (%) | | Impurities at T = 1 month (%) | |
| Sample | LSI | Total | LSI | Total | LSI | Total | LSI | Total | LSI | Total | LSI | Total |
| 1 | 0.26 | 0.37 | 0.29 | 0.42 | 0.33 | 0.43 | 0.12 | 0.22 | 0.11 | 0.20 | 0.12 | 0.19 |
| 2 | 0.26 | 0.37 | 0.24 | 0.35 | 0.31 | 0.53 | 0.12 | 0.12 | 0.13 | 0.18 | 0.11 | 0.11 |
| 3 | 0.27 | 0.27 | 0.27 | 0.41 | 0.33 | 0.45 | 0.12 | 0.17 | 0.12 | 0.22 | 0.11 | 0.17 |
| 4 | 0.28 | 0.28 | 0.23 | 0.34 | 0.36 | 0.47 | 0.12 | 0.17 | 0.12 | 0.23 | 0.11 | 0.11 |
| 5 | 0.27 | 0.38 | 0.26 | 0.41 | 0.31 | 0.42 | 0.11 | 0.11 | 0.12 | 0.26 | 0.11 | 0.16 |
| 6 | 0.26 | 0.39 | 0.27 | 0.41 | 0.33 | 0.75 | 0.10 | 0.10 | 0.15 | 0.31 | 0.12 | 0.17 |
| 7 | 0.26 | 0.26 | 0.26 | 0.41 | 0.32 | 0.56 | 0.13 | 0.18 | 0.12 | 0.29 | 0.12 | 0.17 |
| 8 | 0.25 | 0.35 | 0.26 | 0.42 | 0.32 | 0.56 | 0.09 | 0.09 | 0.11 | 0.23 | 0.11 | 0.22 |
| 9 | 0.20 | 0.30 | 0.25 | 0.38 | 0.29 | 0.29 | 0.10 | 0.15 | 0.12 | 0.17 | 0.11 | 0.16 |
| 10 | 0.26 | 0.26 | 0.29 | 0.44 | 0.32 | 0.57 | 0.12 | 0.12 | 0.15 | 0.28 | 0.10 | 0.16 |
| 11 | 0.26 | 0.26 | 0.31 | 0.51 | 0.29 | 0.57 | 0.13 | 0.17 | 0.13 | 0.29 | 0.24 | 0.49 |
| 12 | 0.22 | 0.34 | 0.26 | 0.39 | 0.27 | 0.27 | 0.13 | 0.27 | 0.12 | 0.33 | 0.11 | 0.17 |
| 13 | 0.26 | 0.38 | 0.26 | 0.41 | 0.31 | 0.43 | 0.10 | 0.19 | 0.12 | 0.27 | 0.15 | 0.22 |
| 14 | 0.26 | 0.37 | 0.25 | 0.41 | 0.31 | 0.44 | 0.11 | 0.16 | 0.13 | 0.34 | 0.15 | 0.34 |
| 15 | 0.20 | 0.32 | 0.24 | 0.39 | 0.27 | 0.27 | 0.10 | 0.15 | 0.13 | 0.35 | 0.11 | 0.23 |
| 16 | 0.25 | 0.38 | 0.26 | 0.39 | 0.55 | 0.86 | 0.11 | 0.11 | 0.12 | 0.27 | 0.14 | 0.26 |
| 17 | 0.00 | 0.00 | 0.00 | 0.00 | 0.00 | 0.00 | 0.13 | 0.23 | 0.12 | 0.23 | 0.12 | 0.26 |
| 18 | 0.27 | 0.41 | 0.28 | 0.45 | 0.27 | 0.79 | 0.00 | 0.00 | 0.00 | 0.00 | 0.00 | 0.00 |
| 19 | 0.27 | 0.41 | 0.26 | 0.42 | 0.32 | 0.46 | 0.11 | 0.27 | 0.13 | 0.48 | 0.17 | 0.34 |
| 20 | 0.17 | 0.44 | 0.22 | 0.55 | 0.35 | 0.60 | 0.12 | 0.21 | 0.13 | 0.28 | 0.12 | 0.23 |

LSI: Largest single impurity

Example 5

Evaluation of the 5-HTP/Low-Dose Carbidopa Gastroretentive Tablets in Human Healthy Volunteers The "fast" 5-HTP (250 mg)/low-dose carbidopa (0.625 mg, 2.5 mg, 5 mg, or 15 mg) gastroretentive tablets were administered orally to subjects from a cohort totaling 16 healthy subjects in a 5-period open label pharmacokinetics study. See Table 9. The subjects' mean age was ~50 years (33 to 60 years). All were Caucasian, 11 males, 5 females. Average weight was ~80 kg and all body mass index (BMI)<32.0 kg/m$^2$. The subjects were admitted to a clinic during the study. The swelling layer of the tablets was radiolabelled with ≤1 MBq $^{111}$In to allow for parallel scintigraphic location of the tablets in the gastrointestinal tract. The tablets were administered in the morning, one tablet per administration, after ingestion of ≥80% of the breakfast. Tablets were administered with 210 mL water followed by a radiolabelled drink (radiocontrast) containing NMT 4 MBq technetium-99m-diethylene triaminepentaacetic acid (99mTc-DTPA) in 30 mL of water. Blood samples for 5-HTP and carbidopa plasma analysis were collected at pre-defined timepoints over 36 h after tablet administration.

In the first 4 periods, the tablets were administered after a standardized FDA high-fat, high-calorie meal (FDA, 2022), in order of increasing doses of carbidopa. Administration of the highest carbidopa dose tablets, 5-HTP (250 mg)/carbidopa 15 mg, were repeated in period 5, but with an FDA medium-fat, medium-calorie meal to assess the impact of an alternative meal type on the 5-HTP and carbidopa pharmacokinetics of the "fast" gastroretentive tablets. See Table 9, below. The 5-HTP and carbidopa in the plasma were analyzed by liquid-chromatography-mass spectrometry. As reference to the tablet 5-HTP profiles, the tablet pharmacokinetics 5-HTP data from the "fast" gastroretentive tablets was compared to plasma 5-HTP data from a separate cohort of 12 healthy volunteers, recruited from the same geographical area, administered 250 mg of native 5-HTP immediate release after a standardized FDA high-fat, high-calorie meal in an analogously designed study, in the same clinic, under the experimental conditions as for the "fast" gastroretentive tablets.

TABLE 9

Pharmacokinetics study periods.

| Period | 5-HTP/low-dose carbidopa gastroretentive tablets | Prandial state |
|---|---|---|
| 1 | 5-HTP/carbidopa gastroretentive prototype 1 tablet, 250 mg 5-HTP, 0.625 mg carbidopa, radiolabelled with NMT 1 MBq $^{111}$In | Fed (high-fat/ high-calorie breakfast) |
| 2 | 5-HTP/carbidopa gastroretentive prototype 2 tablet, 250 mg 5-HTP, 2.5 mg carbidopa, radiolabelled with NMT 1 MBq $^{111}$In | Fed (high-fat/ high-calorie breakfast) |
| 3 | 5-HTP/carbidopa gastroretentive prototype 3 tablet, 250 mg 5-HTP, 5 mg carbidopa, radiolabelled with NMT 1 MBq $^{111}$In | Fed (high-fat/ high-calorie breakfast) |
| 4 | 5-HTP/carbidopa gastroretentive prototype 4 tablet, 250 mg 5-HTP, 15 mgcarbidopa, radiolabelled with NMT 1 MBq $^{111}$In | Fed (high-fat/ high-calorie breakfast) |
| 5 | 5-HTP/carbidopa gastroretentive prototype 4 tablet, 250 mg 5-HTP, 15 mg carbidopa, radiolabelled with NMT 1 MBq $^{111}$In | Fed (moderate-fat/ Moderate-calorie breakfast) |

NMT: not more than.

Figures 6A, 6B:
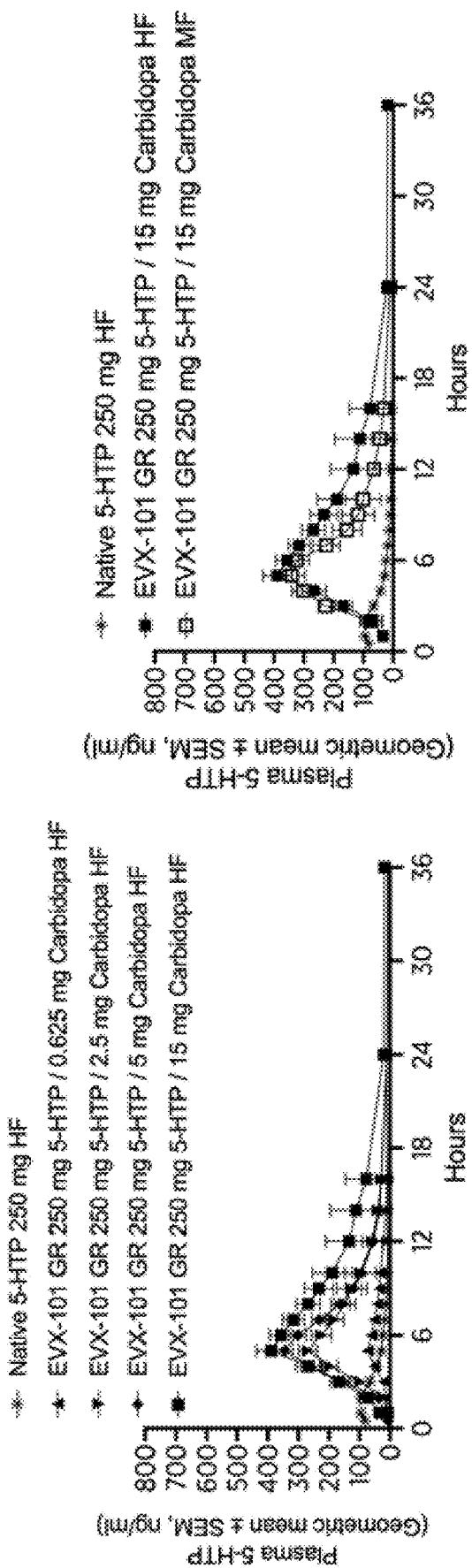
FIGS. 6A-6D: Pharmacokinetic evaluation of the 5-HTP/low-dose carbidopa gastroretentive tablets in human healthy volunteers—5-HTP plasma profiles. Comparison to 250 mg native 5-HTP immediate release after a high-fat, high-calorie (HF) meal.
Figures 6C, 6D:
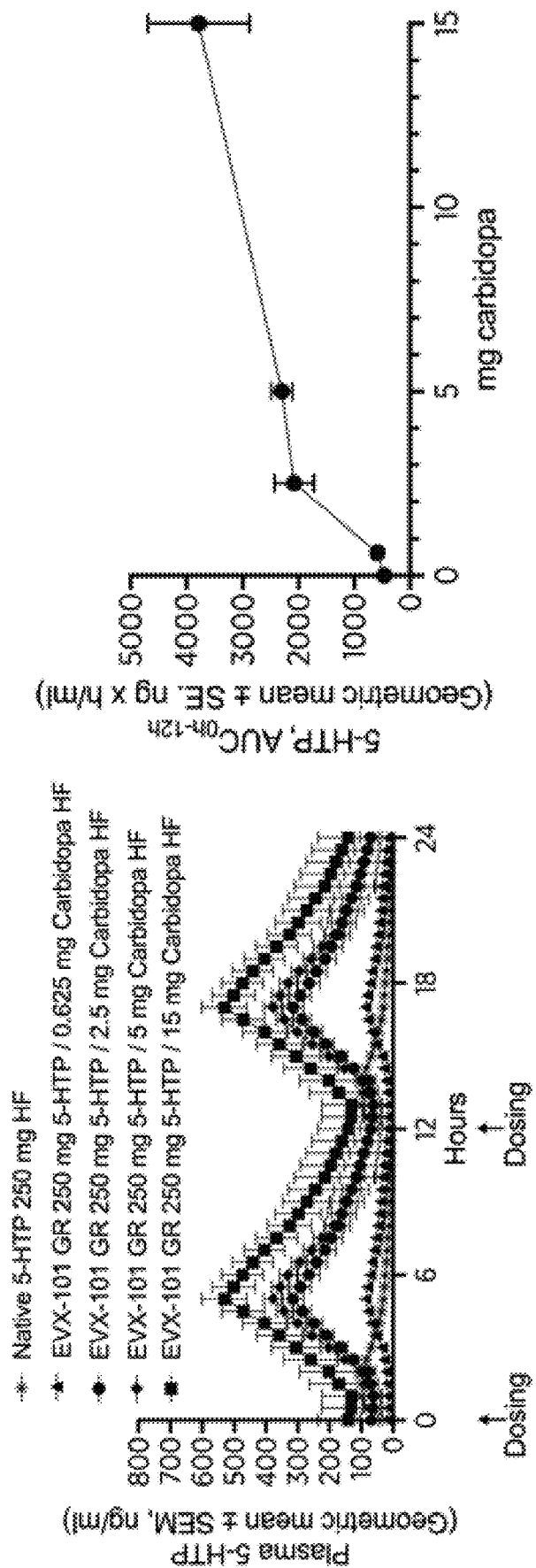
Figures 7A, 7B:
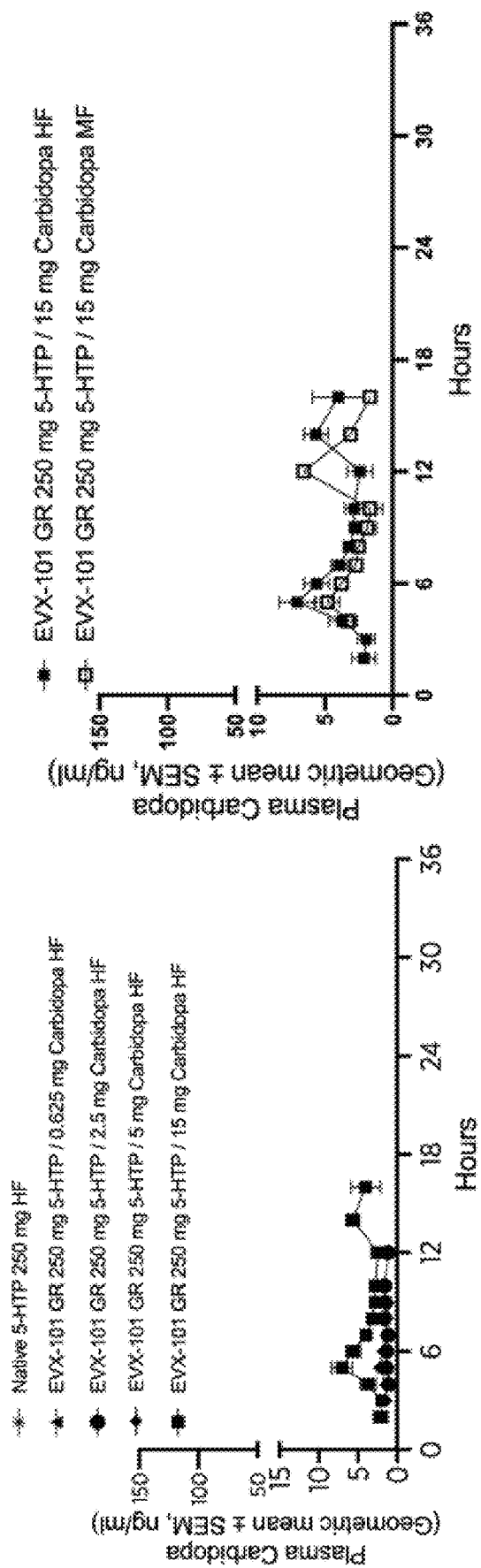
FIGS. 7A-7D: Pharmacokinetic evaluation of the 5-HTP/low-dose carbidopa gastroretentive tablets in human healthy volunteers—carbidopa plasma profiles. Note, absence of data for a given carbidopa dose level indicates insufficient data above the lower limit of quantitation.
Figures 7C, 7D:
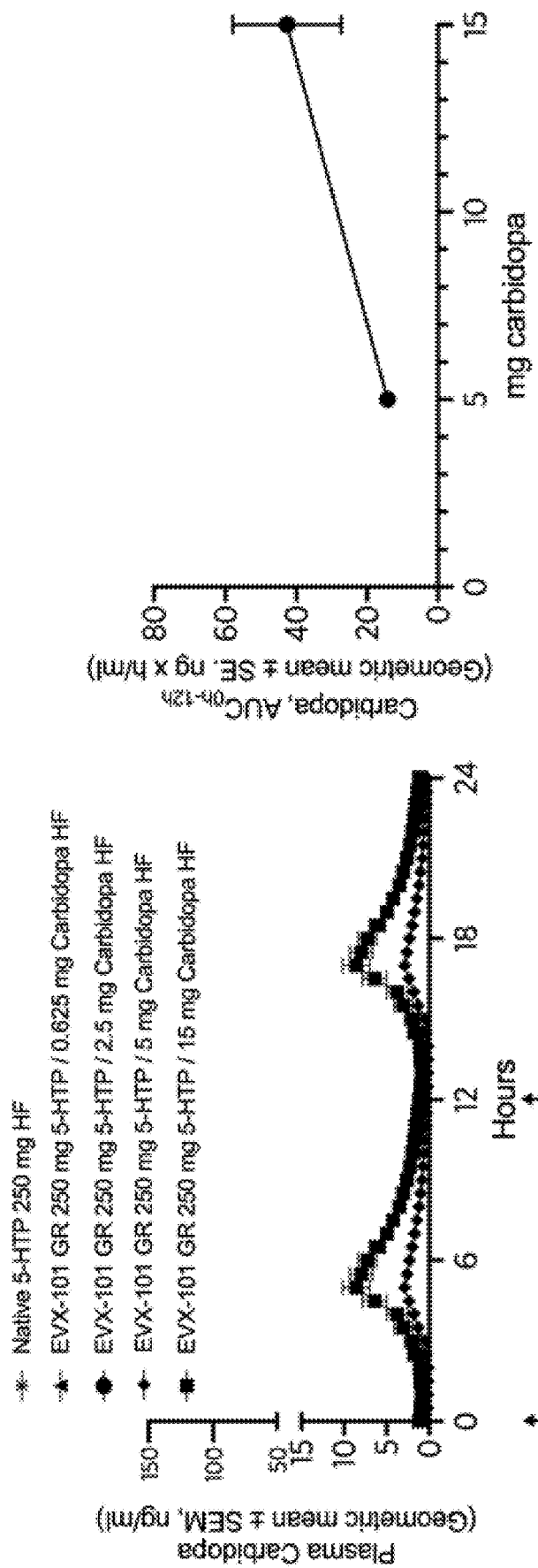

Plasma pharmacokinetics parameters were estimated using standard Phoenix WinNonlin methods. Data are presented as geometric mean±SEM. The 5-HTP plasma profiles after single tablet administration following a high-fat meal are shown in FIG. 6A. The 5-HTP plasma profiles after single tablet administration of "fast" 5-HTP (250 mg)/low-dose carbidopa (15 mg) tablets following either an FDA high-fat high-calorie meal versus after an FDA moderate-fat, moderate-calorie meal are shown in FIG. 6B. Data from periods 1-4 were fit and simulated to extrapolate to pharmacokinetic steady-state at twice-daily dosing (after high-fat, high-calorie meal) using non-parametric superposition. See FIG. 6C. The corresponding AUC$_{1-12\,h}$ at steady-state at twice-daily dosing extrapolated using non-parametric superposition are shown in FIG. 6D. Table 10, below, summarizes key 5-HTP pharmacokinetic parameters after the 5 gastroretentive tablet treatments: (i) native 5-HTP immediate release, (ii) "fast" 5-HTP (250 mg)/low-dose carbidopa (0.625 mg) gastroretentive tablets, (iii) "fast" 5-HTP (250 mg)/low-dose carbidopa (2.5 mg) gastroretentive tablets, (iv) "fast" 5-HTP (250 mg)/low-dose carbidopa (5 mg) gastroretentive tablets, and (v) "fast" 5-HTP (250 mg)/low-dose carbidopa (15 mg) gastroretentive tablets.

TABLE 10

Key pharmacokinetic parameters for 5-HTP/low-dose carbidopa gastroretentive tablets administered to human healthy volunteers. Comparison to native 5-HTP immediate release. Data are geometric means.

| Pharmacokinetic Parameters 5-HTP | Administration | Native 5-HTP immediate release 250 mg | "Fast" 5-HTP (250 mg)/low-dose carbidopa (0.625 mg) gastroretentive tablets | "Fast" 5-HTP (250 mg)/low-dose carbidopa (2.5 mg) gastroretentive tablets | "Fast" 5-HTP (250 mg)/low-dose carbidopa (5 mg) gastroretentive tablets | "Fast" 5-HTP (250 mg)/low-dose carbidopa (15 mg) gastroretentive tablets | Enhancing effect of "Fast" 5-HTP (250 mg)/low-dose carbidopa (15 mg) gastroretentive tablets vs native 5-HTP immediate release 250 mg |
|---|---|---|---|---|---|---|---|
| Exposure relative to immediate release exposure ($AUC_{0\,h-12\,h}$ gastroretentive/ $AUC_{0\,h-12\,h}$ immediate release) | Single | 1 | 1.2 | 3.8 | 4.4 | 6.3 | 5.3-fold increase |
| $T_{Max}$ (Average) | Single | 1 h | 5 h | 5 h | 5 h | 5 h | 4-fold delay |
| Elimination half-life (Average) | Single | 2.9 h | 3.3 h | 4.9 | 5 | 4.4 | 0.5-fold increase |
| Relative steady-state average plasma exposure (average ng/ml gastroretentive/ average ng/ml immediate release) | Steady-state at twice-daily administration (PK simulation by non-parametric superposition) | 1 | 1.3 | 4.5 | 5 | 8.2 | 7.2-fold increase |

Plasma pharmacokinetics data for carbidopa are presented in FIGS. 7A-7D. Carbidopa plasma was below lower limit of quantification (1 ng/ml) at all timepoints at the 0.625 mg carbidopa dose strength, and for most time points at the 2.5 mg carbidopa dose strength. Only for the 5 mg and 15 mg carbidopa dose strengths were extrapolation to steady state using non-parametric superposition possible. Table 11, below, summarizes key carbidopa pharmacokinetic parameters after (i) "fast" 5-HTP (250 mg)/low-dose carbidopa (2.5 mg) gastroretentive tablets, (ii) "fast" 5-HTP (250 mg)/low-dose carbidopa (5 mg) gastroretentive tablets, and (iii) "fast" 5-HTP (250 mg)/low-dose carbidopa (15 mg) gastroretentive tablets, and (iv) "fast" 5-HTP (250 mg)/low-dose carbidopa (15 mg) gastroretentive tablets, the latter following a moderate fat diet. Carbidopa concentrations below the limit of quantification are not summarized in the table. $T_{max}$ of about 5 hours was similar for all dose groups.

TABLE 11

Key pharmacokinetic parameters for carbidopa following single-administration of 5-HTP/low-dose carbidopa gastroretentive tablets in human healthy volunteers. Data are geometric means.

| | Treatment | | | |
|---|---|---|---|---|
| | 250 mg 5-HTP/2.5 mg carbidopa HF | 250 mg 5-HTP/5 mg carbidopa HF | 250 mg 5-HTP/15 mg carbidopa HF | 250 mg 5-HTP/15 mg carbidopa MF |
| $T_{Max}{}^a$ (h) | 5.000 (5.00-10.0) [n = 9] | 5.000 (4.00-6.00) | 5.000 (5.00-16.02) | 5.000 (3.00-9.00) |
| $C_{Max}$ (ng/mL) | 1.35 (22.7%) [n = 9] | 2.36 (26.5%) | 8.07 (52.9%) | 5.43 (59.9%) |
| $T\frac{1}{2}$ (h) | NC | 2.394 (86.7%) [n = 5] | 2.003 (20.6%) [n = 10] | 1.987 (10.3%) [n = 8] |

Figure 8:
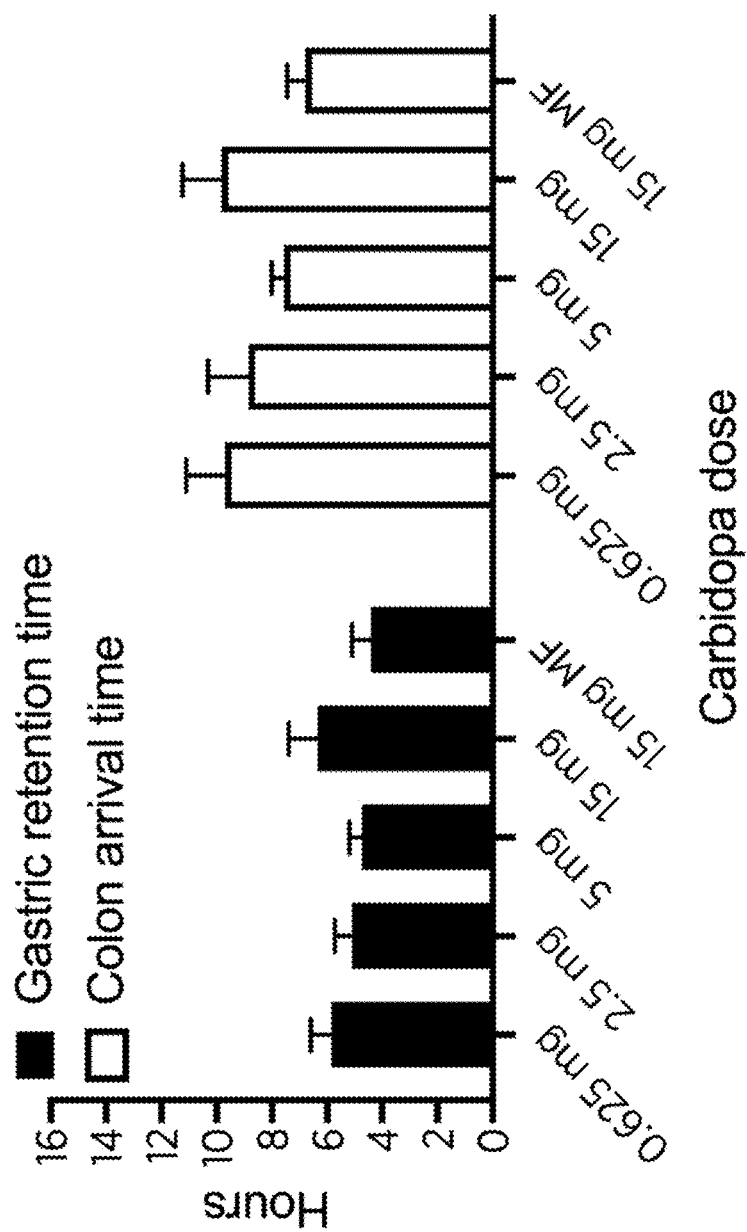
FIG. 8: Gastric retention and colon arrival time of the 5-HTP/low-dose carbidopa gastroretentive tablets in human healthy volunteers.

Using scintigraphy and 111In radio-labelling of the swelling layer, the gastric emptying time and time to colon arrival were estimated by periodic scintigraphic imaging of the subjects following administration of the gastroretentive tablets. See FIG. 8. On average, the tablets were gastric retained in the stomach for about 5 hours, with colon arrival about 9 hours. Single-administration of "fast" 5-HTP (250 mg)/low-dose carbidopa (15 mg) after a moderate-fat, moderate-calorie meal resulted in gastrointestinal transit of the radio-labeled tablet occurring slightly faster than was measured after a high-fat high-calorie meal. The mean gastric emptying time (4.4 hours) and colon arrival (6.3 hours) times were approximately 1-2 hours faster after a moderate-fat moderate-calorie meal than after a high-fat high-calorie meal, when comparing across all 5 administration periods.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

Allen G F, Land J M, Heales S J (2009). A new perspective on the treatment of aromatic L-amino acid decarboxylase deficiency. *Mol Genet Metab* 97(1): 6-14.

Birdsall T C (1998). 5-Hydroxytryptophan: a clinically-effective serotonin precursor. *Altern Med Rev* 3(4): 271-280.

Bono G, Micieli G, Sances G, Calvani M, Nappi G (1984). L-5HTP treatment in primary headaches: an attempt at clinical identification of responsive patients. *Cephalalgia* 4(3): 159-165.

Cangiano C, Ceci F, Cascino A, Del Ben M, Laviano A, Muscaritoli M, et al (1992). Eating behavior and adherence to dietary prescriptions in obese adult subjects treated with 5-hydroxytryptophan. *Am J Clin Nutr* 56(5): 863-867.

Caruso I, Sarzi Puttini P, Cazzola M, Azzolini V (1990). Double-blind study of 5-hydroxytryptophan versus placebo in the treatment of primary fibromyalgia syndrome. *The Journal of international medical research* 18(3): 201-209.

Donnelly, Ronald F (2016) Stability of Levodopa/Carbidopa Rectal Suspensions. *Hosp Pharm.* December; 51(11): 915-921.

Eisenhofer G, Brown S, Peitzsch M, Pelzel D, Lattke P, Glockner S, et al (2014). Levodopa therapy in Parkinson's disease: influence on liquid chromatographic tandem mass spectrometric-based measurements of plasma and urinary normetanephrine, metanephrine and methoxytyramine. *Ann Clin Biochem* 51 (Pt 1): 38-46.

FDA (2022). Assessing the Effects of Food on Drugs in INDs and NDAs—Clinical Pharmacology Considerations Guidance for Industry.

Garfinkel P E, Warsh J J, Stancer H C, Godse D D, Brown G M, Vranic M (1977). The effect of a peripheral decarboxylase inhibitor (carbidopa) on monoamine and neuroendocrine function in man. *Neurology* 27(5): 443-447.

Gijsman H J, van Gerven J M, de Kam M L, Schoemaker R C, Pieters M S, Weemaes M, et al (2002). Placebo-controlled comparison of three dose-regimens of 5-hydroxytryptophan challenge test in healthy volunteers. *J Clin Psychopharmacol* 22(2): 183-189.

Haddad, P (1998) The SSRI discontinuation syndrome. *J Psychopharmacol.* 12(3):305-13. Jacobsen J P, Rudder M L, Roberts W, Royer E L, Robinson T J, Oh A, et al (2016a). SSRI Augmentation by 5-Hydroxytryptophan Slow Release: Mouse Pharmacodynamic Proof of Concept. *Neuropsychopharmacology* 41(9): 2324-2334.

Jacobsen J P R, Krystal A D, Krishnan K R R, Caron M G (2016b). Adjunctive 5-Hydroxytryptophan Slow-Release for Treatment-Resistant Depression: Clinical and Preclinical Rationale. *Trends Pharmacol Sci* 37(11): 933-944.

Jacobsen J P R, Oh A, Bangle R, Roberts W L, Royer E L, Modesto N, et al (2019). Slow-release delivery enhances the pharmacological properties of oral 5-hydroxytryptophan: mouse proof-of-concept. *Neuropsychopharmacology* 44(12): 2082-2090.

Kahn R S, Westenberg H G (1985). L-5-hydroxytryptophan in the treatment of anxiety disorders. *J Affect Disord* 8(2): 197-200.

Lowe S L, Yeo K P, Teng L, Soon D K, Pan A, Wise S D, et al (2006). L-5-Hydroxytryptophan augments the neuroendocrine response to a SSRI. *Psychoneuroendocrinology* 31(4): 473-484.

Magnussen I, Dupont E, Prange-Hansen A, de Fine Olivarius B (1977). Palatal myoclonus treated with 5-hydroxytryptophan and a decarboxylase-inhibitor. *Acta Neurol Scand* 55(3): 251-253.

Magnussen I, Mondrup K, Engbaek F, Lademann A, Olivarius B D (1982). Treatment of myoclonic syndromes with paroxetine alone or combined with 5-HTP. *Acta Neurol Scand* 66(2): 276-282.

Meloni M, Puligheddu M, Carta M, Cannas A, Figorilli M, Defazio G (2020a). Efficacy and safety of 5-hydroxytryptophan on depression and apathy in Parkinson's disease: a preliminary finding. *Eur J Neurol* 27(5): 779-786.

Meloni M, Puligheddu M, Sanna F, Cannas A, Farris R, Tronci E, et al (2020b). Efficacy and safety of 5-Hydroxytryptophan on levodopa-induced motor complications in Parkinson's disease: A preliminary finding. *J Neurol Sci* 415: 116869.

Meltzer H, Bastani B, Jayathilake K, Maes M (1997). Fluoxetine, but not tricyclic antidepressants, potentiates the 5-hydroxytryptophan-mediated increase in plasma cortisol and prolactin secretion in subjects with major depression or with obsessive compulsive disorder. *Neuropsychopharmacology* 17(1): 1-11.

PCT Publication No. WO 2019/245925 by Jacobsen et al.

Ramaekers V T, Senderek J, Hausler M, Haring M, Abeling N, Zerres K, et al (2001). A novel neurodevelopmental syndrome responsive to 5-hydroxytryptophan and carbidopa. *Molecular genetics and metabolism* 73(2): 179-187.

Rauws A G, Vos J G, Garbis-Berkvens J M, Peters P W, de Vries T, van Logten M J (1982). Comparative 90-day toxicity of two decarboxylase inhibitors, benserazide and carbidopa, in the rat. *Toxicol Appl Pharmacol* 66(2): 201-220.

Santucci M, Cortelli P, Rossi P G, Baruzzi A, Sacquegna T (1986). L-5-hydroxytryptophan versus placebo in childhood migraine prophylaxis: a double-blind crossover study. *Cephalalgia* 6(3): 155-157.

Sargent P A, Williamson D J, Cowen P J (1998). Brain 5-H T neurotransmission during paroxetine treatment. *Br J Psychiatry* 172: 49-52.

Shenker Y, Gross M D, Grekin R J (1985). Central serotonergic stimulation of aldosterone secretion. *J Clin Invest* 76(4): 1485-1490.

Thombre A G (2005). Assessment of the feasibility of oral controlled release in an exploratory development setting. *Drug Discov Today* 10(17): 1159-1166.

Trouillas P, Brudon F, Adeleine P (1988). Improvement of cerebellar ataxia with levorotatory form of 5-hydroxytryptophan. A double-blind study with quantified data processing. *Arch Neurol* 45(11): 1217-1222.

Turner E H, Loftis J M, Blackwell A D (2006). Serotonin a la carte: supplementation with the serotonin precursor 5-hydroxytryptophan. *Pharmacol Ther* 109(3): 325-338.

U.S. Pat. No. 9,161,911 to Hou.

U.S. Pat. No. 11,337,963 to Jacobsen et al.

van Hiele L J (1980). 1-5-Hydroxytryptophan in depression: the first substitution therapy in psychiatry? The treatment of 99 out-patients with 'therapy-resistant' depressions. *Neuropsychobiology* 6(4): 230-240.

van Praag H M (1982). Serotonin precursors in the treatment of depression. *Adv Biochem Psychopharmacol* 34: 259-286.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A gastroretentive dosage form comprising a bilayer tablet, wherein said tablet comprises two layers:
   (a) a swelling layer comprising one or more hydrophilic polymers, wherein each of said one or more hydrophilic polymers is swellable in the presence of gastric fluid; and
   (b) a modified release layer, wherein the modified release layer comprises one or more hydrophilic polymers, 5-hydroxytryptophan (5-HTP) and carbidopa; and
      (i) wherein the dosage form provides sustained release of both the 5-HTP and the carbidopa upon administration of the tablet to a mammalian subject;
      (ii) wherein, in dissolution testing in a USP Apparatus III: (1) a time period over which 80% by weight of the 5-HTP releases from the dosage form (T=80% (5-HTP)) is about 4 hours to about 13.6 hours, and (2) T=80%(5-HTP) and a time period over which 80% by weight of the carbidopa releases from the dosage form (T=80%$_{(carbidopa)}$) differ by less than 2 hours; and
      (iii) wherein the tablet comprises about 250 mg of 5-HTP and about 0.3125 mg to about 25 mg of carbidopa.

2. The gastroretentive dosage form of claim 1, wherein one or both of T=80%$_{(5-HTP)}$ and T=80%$_{(carbidopa)}$ in dissolution testing in a USP Apparatus III are about 5 hours to about 12 hours.

3. The gastroretentive dosage form of claim 1, wherein the one or more hydrophilic polymers of the modified release layer are each selected from the group consisting of a low viscosity hydroxypropyl methylcellulose (HPMC), medium viscosity HPMC, high viscosity HPMC, low molecular weight (MW) polyethylene oxide (PEO), medium MW PEO, high MW PEO, and high viscosity hydroxyethyl cellulose.

4. The gastroretentive dosage form of claim 3, wherein the modified release layer comprises about 14% (w/w) to about 37% (w/w) of the one or more hydrophilic polymers based on a total weight of the modified release layer.

5. The gastroretentive dosage form of claim 3, wherein the modified release layer comprises about 5% (w/w) of a medium MW PEO or a high MW PEO and about 13% (w/w) to about 32% (w/w) of a low viscosity HMPC, a medium viscosity HPMC, or a mixture of medium viscosity HPMC and high viscosity HPMC based on a total weight of the modified release layer.

6. The gastroretentive dosage form of claim 1, wherein the modified release layer further comprises about 5% (w/w) to about 30% (w/w) of one or more ductile filler based on a total weight of the modified release layer.

7. The gastroretentive dosage form of claim 1, wherein the modified release layer further comprises about 0.5% (w/w) to about 3% (w/w) of a lubricant based on a total weight of the modified release layer.

8. The gastroretentive dosage form of claim 1, wherein the modified release layer further comprises about 0.01% (w/w) to about 1% (w/w) of an antioxidant based on a total weight of the modified release layer.

9. The gastroretentive dosage form of claim 1, wherein the swelling layer comprises high MW PEO and high viscosity HPMC.

10. The gastroretentive dosage form of claim 1, wherein the swelling layer further comprises up to about 5% (w/w) of a lubricant based on a total weight of the swelling layer.

11. The gastroretentive dosage form of claim 1, wherein the swelling layer and the modified release layer have about the same weight.

12. The gastroretentive dosage form of claim 1, wherein a total weight of the tablet is about 500 milligrams (mg) to about 2000 mg.

13. The gastroretentive dosage form of claim 1, wherein the modified release layer comprises, based on a total weight of the modified release layer: about 50% (w/w) 5-HTP; about 0.06% (w/w) to about 5.4% (w/w) carbidopa; about 5.7% (w/w) to about 25.1% (w/w) microcrystalline cellulose (MCC); about 5% (w/w) medium or high MW PEO; about 7% (w/w) to about 18% (w/w) medium viscosity HPMC; about 0% (w/w) to about 25% (w/w) high viscosity HPMC; about 0.2% (w/w) butylated hydroxytoluene (BHT), about 0.1% (w/w) colloidal silica; and about 1.5% (w/w) sodium stearyl fumarate (SSF).

14. The gastroretentive dosage form of claim 13, wherein the modified release layer comprises, based on a total weight of the modified release layer: about 50% (w/w) 5-HTP; about 0.06% (w/w) to about 5.4% (w/w) carbidopa; about 19.8% (w/w) to about 25.1% (w/w) MCC; about 5% (w/w) medium or high MW PEO; about 18% (w/w) medium viscosity HPMC; about 0.2% (w/w) BHT, about 0.1% (w/w) colloidal silica; and about 1.5% (w/w) SSF.

15. The gastroretentive dosage form of claim 1, wherein the swelling layer swells to at least about 150% of the dry volume of the swelling layer in an aqueous solution.

16. The gastroretentive dosage form of claim 1, wherein the tablet remains in the stomach for about 5 hours after oral administration to a human.

17. The gastroretentive dosage form of claim 1, wherein the modified release layer remains chemically stable for at least 70 days when stored at about 15° C. to about 25° C. protected from light.

18. The gastroretentive dosage form of claim 1, wherein the modified release layer and the swelling layer remain attached to one another for at least 8 hours during disintegration testing according to USP <701> with use of a disk.

19. The gastroretentive dosage form of claim 1, wherein the modified release layer has an acceptance value (AV) of about 15 or less and a relative standard deviation (RSD) of about 3 or less in content uniformity testing according to USP <905>.

20. The gastroretentive dosage form of claim 1, wherein administration of the tablet once or twice daily to a mammalian subject provides a time to achieve a maximum plasma concentration ($T_{Max}$) of 5-HTP that is delayed about 4 hours on average compared to an immediate release dosage form of native 5-HTP.

21. The gastroretentive dosage form of claim 1, wherein administration of the tablet once or twice daily to a mammalian subject provides about 1-fold to about 10-fold 5-HTP plasma exposure compared to an immediate release dosage form of native 5-HTP comprising the same weight of 5-HTP as said tablet and wherein said immediate release dosage form of native 5-HTP does not comprise carbidopa.

22. The gastroretentive dosage form of claim 1, wherein administration of the tablet once or twice daily to a mammalian subject provides a steady state average 5-HTP plasma level of about 25 nanograms per milliliter (ng/ml) or more.

23. The gastroretentive dosage form of claim 1, wherein administration of the tablet once or twice daily to a mammalian subject provides a steady state average carbidopa plasma level of about 25 ng/ml or less.

24. The gastroretentive dosage form of claim 1, wherein administration of the tablet once or twice daily to a mammalian subject provides a steady state average maximum carbidopa plasma level ($C_{Max}$) of about 25 ng/ml or less.

25. The gastroretentive dosage form of claim 1, wherein administration of the tablet once or twice daily to a mammalian subject provides an increased 5-HTP half-life compared to a 5-HTP half-life when native 5-HTP is administered in an immediate release form.

26. The gastroretentive dosage form of claim 1, wherein the dosage form is configured to provide a same release rate for 5-HTP and/or a same release rate for carbidopa over a range of carbidopa content from 0.3125 mg to 25 mg when a total combined weight of carbidopa and microcrystalline cellulose is held constant.

27. The gastroretentive dosage form of claim 1, wherein administration of the dosage form to a human subject provides an average time to achieve maximum plasma concentration ($T_{Max}$) for 5-HTP of about 4 hours to 8 hours.

28. The gastroretentive dosage form of claim 1, wherein administration of the dosage form to a human subject provides an average time to achieve maximum plasma concentration ($T_{Max}$) for both 5-HTP and carbidopa of about 5 hours.

* * * * *